(12) United States Patent
Otvos et al.

(10) Patent No.: US 11,037,683 B2
(45) Date of Patent: *Jun. 15, 2021

(54) MULTIPLE-MARKER RISK PARAMETERS PREDICTIVE OF CONVERSION TO DIABETES

(71) Applicant: LipoScience, Inc., Morrisville, NC (US)

(72) Inventors: James D. Otvos, Cary, NC (US); Irina Y. Shalaurova, Cary, NC (US)

(73) Assignee: LipoScience, Inc., Morrisville, NC (US)

( * ) Notice: Subject to any disclaimer, the term of this patent is extended or adjusted under 35 U.S.C. 154(b) by 719 days.

This patent is subject to a terminal disclaimer.

(21) Appl. No.: 15/880,170

(22) Filed: Jan. 25, 2018

(65) Prior Publication Data

US 2018/0158554 A1 Jun. 7, 2018

Related U.S. Application Data

(63) Continuation of application No. 14/589,793, filed on Jan. 5, 2015, now Pat. No. 9,928,345, which is a
(Continued)

(51) Int. Cl.
*G01N 33/48* (2006.01)
*G01N 33/50* (2006.01)
(Continued)

(52) U.S. Cl.
CPC ........... *G16H 50/30* (2018.01); *A61B 5/4842* (2013.01); *A61B 5/7275* (2013.01); *G01N 24/08* (2013.01); *G01R 33/465* (2013.01); *A61B 5/055* (2013.01)

(58) Field of Classification Search
CPC .... G16H 50/30; A61B 5/4842; A61B 5/7275; A61B 5/055; G01N 24/08; G01R 33/465
See application file for complete search history.

(56) References Cited

U.S. PATENT DOCUMENTS

| 4,529,710 A | 7/1985 | Spicer et al. |
| 4,933,844 A | 6/1990 | Otvos |

(Continued)

FOREIGN PATENT DOCUMENTS

| CN | 104520699 | 4/2015 |
| CN | 104823055 | 8/2015 |

(Continued)

OTHER PUBLICATIONS

Barclay, A. et al., 'Glycemic index, glycemic load, and chronic disease risk-a meta-analysis of observational studies', The American Journal of Clinical Nutrition, 2008, vol. 87, No. 3, pp. 627-637.
(Continued)

*Primary Examiner* — Russell S Negin
(74) *Attorney, Agent, or Firm* — Kilpatrick Townsend & Stockton LLP

(57) ABSTRACT

Methods, systems and circuits evaluate a subject's risk of developing type 2 diabetes using defined mathematical models of short term risk (STR) and longer term risk of progression. The evaluations can stratify risk for patients having the same glucose measurement, particularly those with intermediate or low (normal) fasting plasma glucose (FPG) values. The STR or IR (insulin resistance) model(s) may include an inflammatory biomarker such as an NMR derived measurements of GlycA and a plurality of selected lipoprotein components of at least one biosample of the subject. Embodiments of the invention also provide methods, systems and circuits that generate STR scores as a marker of beta-cell dysfunction or impairment.

20 Claims, 26 Drawing Sheets
(3 of 26 Drawing Sheet(s) Filed in Color)

Related U.S. Application Data continuation-in-part of application No. PCT/US2013/044679, filed on Jun. 7, 2013, which is a continuation-in-part of application No. 13/830,784, filed on Mar. 14, 2013, now Pat. No. 9,361,429.

(60) Provisional application No. 61/923,855, filed on Jan. 6, 2014, provisional application No. 61/739,305, filed on Dec. 19, 2012, provisional application No. 61/711,471, filed on Oct. 9, 2012, provisional application No. 61/657,315, filed on Jun. 8, 2012.

(51) Int. Cl.

| | |
|---|---|
| *G16H 50/30* | (2018.01) |
| *A61B 5/00* | (2006.01) |
| *G01N 24/08* | (2006.01) |
| *G01R 33/465* | (2006.01) |
| *A61B 5/055* | (2006.01) |

(56) References Cited

U.S. PATENT DOCUMENTS

| | | | |
|---|---|---|---|
| 6,518,069 | B1 | 2/2003 | Otvos et al. |
| 6,576,471 | B2 | 6/2003 | Otvos |
| 7,181,348 | B2 | 2/2007 | Wishart et al. |
| 7,191,069 | B2 | 3/2007 | Wishart et al. |
| 7,373,256 | B2 | 5/2008 | Nicholson et al. |
| 7,491,543 | B2 | 2/2009 | Barzilai |
| 7,550,260 | B2 | 6/2009 | Kaddurah-Daouk et al. |
| 7,629,315 | B2 | 12/2009 | Zhao |
| 7,723,050 | B2 | 5/2010 | Urdea et al. |
| 7,923,253 | B2 | 4/2011 | Metz et al. |
| 7,927,878 | B2 | 4/2011 | Kremer et al. |
| 8,119,358 | B2 | 2/2012 | Urdea et al. |
| 8,187,830 | B2 | 5/2012 | Hu et al. |
| 8,367,359 | B1 | 2/2013 | Adams et al. |
| 8,386,187 | B2 | 2/2013 | Otvos |
| 8,409,816 | B2 | 4/2013 | Urdea et al. |
| 8,420,337 | B2 | 4/2013 | Heinecke et al. |
| 8,476,008 | B2 | 7/2013 | Nagalla et al. |
| 9,361,429 | B2 | 6/2016 | Otvos et al. |
| 9,792,410 | B2 | 10/2017 | Otvos et al. |
| 9,928,345 | B2 * | 3/2018 | Otvos ............ G01N 24/08 |
| 10,388,414 | B2 | 8/2019 | Otvos et al. |
| 2003/0119194 | A1 | 6/2003 | Otvos |
| 2004/0058386 | A1 | 3/2004 | Wishart et al. |
| 2005/0074745 | A1 | 4/2005 | Clayton et al. |
| 2005/0222504 | A1 | 10/2005 | Otvos et al. |
| 2008/0026378 | A1 | 1/2008 | Bottazzo et al. |
| 2008/0300170 | A1 | 12/2008 | Gelber et al. |
| 2009/0061475 | A1 | 3/2009 | Berggren |
| 2009/0286324 | A1 | 11/2009 | Metz et al. |
| 2010/0100334 | A1 | 4/2010 | Otvos |
| 2011/0004453 | A1 | 1/2011 | Engelsen et al. |
| 2011/0034035 | A1 | 2/2011 | Liang et al. |
| 2011/0034039 | A1 | 2/2011 | Liang et al. |
| 2011/0111137 | A1 | 5/2011 | Liang et al. |
| 2011/0136241 | A1 | 6/2011 | Naylor |
| 2011/0165781 | A1 | 7/2011 | Liang et al. |
| 2011/0189780 | A1 | 8/2011 | Cerda et al. |
| 2011/0311650 | A1 | 12/2011 | Wang et al. |
| 2012/0122981 | A1 | 5/2012 | Hu et al. |
| 2012/0309030 | A1 | 12/2012 | McKenna et al. |
| 2012/0328594 | A1 | 12/2012 | McKenna et al. |
| 2013/0177544 | A1 | 7/2013 | Stoll et al. |
| 2013/0328561 | A1 * | 12/2013 | Otvos ............ A61B 5/0044 324/309 |
| 2015/0127267 | A1 | 5/2015 | Otvos et al. |
| 2015/0149095 | A1 | 5/2015 | Otvos et al. |
| 2016/0321424 | A1 | 11/2016 | Otvos et al. |

FOREIGN PATENT DOCUMENTS

| | | |
|---|---|---|
| CN | 106461639 | 2/2017 |
| CN | 106461639 | 3/2020 |
| EP | 264 815 | 4/1988 |
| EP | 3 058 369 | 8/2016 |
| IN | 2583/CHENP/2015 | 7/2016 |
| IN | 8937/CHENP/2014 | 7/2016 |
| JP | 2002543392 | 12/2002 |
| JP | 2006317311 | 11/2006 |
| JP | 2007132752 | 5/2007 |
| JP | 2009530627 | 8/2009 |
| JP | 2010534325 | 11/2010 |
| JP | 2012506051 | 3/2012 |
| WO | 2007/110357 | 10/2007 |
| WO | WO 2008/137075 | 11/2008 |
| WO | 2010/114897 | 10/2010 |
| WO | 2011/059720 | 5/2011 |
| WO | 2011/143779 | 11/2011 |
| WO | 2011/153271 | 12/2011 |
| WO | 2012/045773 | 4/2012 |
| WO | 2013/012536 | 1/2013 |
| WO | 2013/184483 | 12/2013 |
| WO | WO 2013/185014 | 12/2013 |
| WO | 2015/103553 | 7/2015 |

OTHER PUBLICATIONS

Lu et al., 'Evaluation of risk equations for prediction of short-term coronary heart disease events in patients with long-standing type 2 diabetes: the Translating Research into Action for Diabetes (TRIAD) study', BMC Endocrine disorders, 2012, vol. 12, Article No. 12 (internal pp. 1-10).

O'Connell, T., 'The complex role of branched chain amino acids in diabetes and cancer', Metabolites, 2013, vol. 3, No. 4, pp. 931-945.

Shalaurova, I. et al., "Lipoprotein Insulin Resistance Index: A Lipoprotein Particle—Derived Measure of Insulin Resistance," Metabolic Syndrome and Related Disorders 12(8):422-429 (2014).

European Patent Application No. 15733142.2, Partial European Search Report dated Apr. 11, 2017.

Patent Cooperation Treaty, International Search Report and Written Opinion, International Application No. PCT/US2015/010184, dated Jan. 5, 2015.

Bell, J.D. et al., "Assignment of Resonances for 'Acute-Phase' Glycoproteins in High Resolution Proton NMR Spectra of Human Blood Plasma", FEBS Letters, 215(2):311-315 (1987).

Chang, L. et al., "NMR Analysis on Gly", Journal of Anhui Agri. Sci., 38(19):9937-9938 (2010).

Delaglio, F. et al., "Measurement of Homonuclear Proton Couplings from Regular 20 COSY Spectra", J. Magnetic Resonance, 149(2):276-281 (2001).

Gao, H. et al., "Metabonomic Profiling of Renal Cell Carcinoma: High-resolution Proton Nuclear Magnetic Resonance Spectroscopy of Human Serum with Multivariate Data Analysis", Anal Chimica Acta., 624(2):269-277 (2008).

Hiltunen, Y. et al., "A Lineshape Fitting Model for $^1$H NMR Spectra of Human Blood Plasma", Magnetic Resonance Med., 21(2):222-232 (1991).

Lanza, I. et al., "Quantitative Metabolomics by $^1$H-NMR and LC-MS/MS Confirms Altered Metabolic Pathways in Diabetes", PloS ONE, 5(6):e10538 (2010).

Liu, et al., "Application of HNMR Technology in Amino Acid Analysis and ATM Degradation Product Detection", Medical Journal of National Defending Forces in Southwest China, 12(3):247-248 (2002).

Moolenaar, S. et al., "Proton Nuclear Magnetic Resonance Spectroscopy of Body Fluids in the Field of Inborn Errors of Metabolism", Ann. Clin. Biochem., 40(1):16-24 (2003).

Nicholson, J. et al., "Proton-Nuclear-Magnetic-Resonance Studies of Serum, Plasma and Urine From Fasting Normal and Diabetic Subjects", Biochem. J., 217(2):365-375 (1984).

Nieuwdorp, M. et al., "Reconstituted HDL Infusion Restores Endothelial Function in Patients with Type 2 Diabetes Mellitus", Diabetologia, 51(6):1081-1084 (2008).

Pauli, G. et al., "Quantitative $^1$H NMR. Development and Potential of an Analytical Method: An Update", J. Nat. Prod. 75(4):834-851 (2012).

(56) References Cited

OTHER PUBLICATIONS

Psychogios, N. et al., "The Human Serum Metabolome", PloS ONE, 6(2):e16957 (2011).
Vitols, C. and Mercier, P., "Correcting Lineshapes in NMR Spectra", Chenomx, Jun. 2006, 5 pages.
Wang, T. et al., "Metabolic Profiles and the Risk of Developing Diabetes", Nat. Med. 17(4):448-453 (2011).
Wei, L. et al., "Toxicological Effects of Cinnabar in Rats by NMR-Based Metabolic Profiling of Urine and Serum", Toxicology and Applied Pharmacology, 227(3):417-429 (2008).
Wishart, D. et al., "The Human Cerebrospinal Fluid Metabolome", J. Chromatogr. B, 871(2):164-173 (2008).
You, L. et al., "Serum Metabonomics Research on Shenxu-tanyu Syndrome Type 2 Diabetes Mellitus Based on NMR", Sci. Techn. Rev., 30(8):25-29 (2012).
U.S. Appl. No. 13/801,604, Final Office Action, dated Dec. 9, 2015, 20 pages.
U.S. Appl. No. 13/801,604, Non-Final Office Action, dated Apr. 28, 2015, 18 pages.
U.S. Appl. No. 13/801,604, Supplemental Non-Final Office Action, dated May 4, 2015, 17 pages.
U.S. Appl. No. 13/830,784, Final Office Action, dated Jun. 11, 2015, 9 pages.
U.S. Appl. No. 13/830,784, Non-Final Office Action, dated Nov. 25, 2014, 8 pages.
U.S. Appl. No. 14/405,852, Non-Final Office Action, dated Oct. 25, 2016, 14 pages.
U.S. Appl. No. 14/589,793, Final Office Action, dated Jun. 8, 2017, 8 pages.
U.S. Appl. No. 14/589,793, Non-Final Office Action, dated Dec. 20, 2016, 10 pages.
U.S. Appl. No. 15/145,409, Final Office Action, dated Nov. 26, 2018, 13 pages.
U.S. Appl. No. 15/145,409, Non-Final Office Action, dated Apr. 6, 2018, 13 pages.
AU 2013271432, First Examiner Report, dated Sep. 14, 2016, 3 pages.
CN 201380041864.1, Office Action, dated Nov. 3, 2016, 10 pages.
CN 201380041864.1, Office Action, dated Mar. 3, 2016, 22 pages.
CN 201380064302.9, Notice of Decision to Grant, dated Aug. 28, 2017, 5 pages.
CN 201380064302.9, Office Action, dated Sep. 19, 2016, 11 pages.
CN 201380064302.9, Office Action, dated Jan. 28, 2016, 15 pages.
CN 201380064302.9, Office Action, dated Mar. 22, 2017, 8 pages.
CN 201580003866.0, Notice of Decision to Grant, dated Nov. 29, 2019, 5 pages.
CN 201580003866.0, Office Action, dated Feb. 25, 2019, 13 pages.
CN 201580003866.0, Office Action, dated Sep. 28, 2017, 16 pages.
CN 201580003866.0, Office Action, dated Jul. 11, 2018, 22 pages.
EP 13800325.6, Extended European Search Report, dated Sep. 8, 2016, 12 pages.
EP 13800325.6, Partial Supplementary European Search Report, dated May 20, 2016, 7 pages.
EP 13844778.4, Extended European Search Report, dated Jun. 1, 2016, 11 pages.
EP 15733142.2, Extended European Search Report, dated Jul. 14, 2017, 12 pages.
EP 15733142.2, Notice of Decision to Grant, dated May 25, 2020, 2 pages.
EP 15733142.2, Office Action, dated Feb. 22, 2019, 3 pages.
EP 15733142.2, Office Action, dated Jun. 18, 2018, 6 pages.
JP 2015-516236, Office Action, dated Oct. 10, 2017, 4 pages.
JP 2015-516236, Office Action, dated Mar. 7, 2017, 6 pages.
JP 2015-536865, Notice of Decision to Grant, dated Nov. 28, 2017, 3 pages.
JP 2015-536865, Office Action, dated May 23, 2017, 7 pages.
JP 2016-562476, Notice of Decision to Grant, dated Mar. 31, 2020, 4 pages.
JP 2016-562476, Office Action, dated Oct. 2, 2018, 15 pages.
JP 2016-562476, Office Action, dated Aug. 6, 2019, 6 pages.
PCT/US2013/044679, International Search Report and Written Opinion, dated Oct. 28, 2013.
PCT/US2013/44679, International Preliminary Report on Patentability, dated Dec. 18, 2014, 13 pages.
PCT/US2015/010184, International Preliminary Report on Patentability, dated Jul. 21, 2016, 12 pages.
SG 11201408002T, Notice of Allowance, dated Dec. 19, 2016, 1 page.
SG 11201408002T, Office Action, dated Apr. 12, 2016, 7 pages.
SG 11201408002T, "Supplementary Examination Report", dated Dec. 12, 2016, 3 pages.

* cited by examiner

NMR HDL SUBPOPULATION GROUPINGS AND NOMENCLATURE FOR DIABETES RISK APPLICATIONS

| HDL DECONVOLUTION MODEL COMPONENTS | | HDL SUBPOPULATIONS | | | DM SUBCLASS GROUPINGS* | |
|---|---|---|---|---|---|---|
| COMPONENT NAME | ESTIMATED DIAMETER (nm) | COMPONENT NAME | SUBPOPULATION NAME | ESTIMATED DIAMETER (nm) | DESCRIPTIVE NAME | SUBCLASS NAMES |
| H1 | 7.4 | $H_{1-2}$ | HP1 | 7.4-7.5 | --- | --- |
| H2 | 7.5 | | | | | |
| H3 | 7.6 | $H_{3-5}$ | HP2 | 7.6-7.9 | SMALL (7.6-8.2 nm) | $HS_{DM}$ |
| H4 | 7.8 | | | | | |
| H5 | 7.9 | | | | | |
| H6 | 8.0 | $H_{6-8}$ | HP3 | 8.0-8.2 | | |
| H7 | 8.1 | | | | | |
| H8 | 8.2 | | | | | |
| H9 | 8.3 | $H_{9-11}$ | HP4 | 8.3-8.5 | MEDIUM (8.3-10.2 nm) | $HM_{DM}$ |
| H10 | 8.4 | | | | | |
| H11 | 8.5 | | | | | |
| H12 | 8.6 | $H_{12-14}$ | HP5 | 8.6-9.3 | | |
| H13 | 9.0 | | | | | |
| H14 | 9.2 | | | | | |
| H15 | 9.4 | $H_{15-17}$ | HP6 | 9.4-10.2 | | |
| H16 | 9.7 | | | | | |
| H17 | 10.0 | | | | | |
| H18 | 10.5 | $H_{18-20}$ | HP7 | 10.3-10.9 | LARGE (>10.2 nm) | $HL_{DM}$ |
| H19 | 10.6 | | | | | |
| H20 | 10.8 | | | | | |
| H21 | 11.0 | $H_{21-23}$ | HP8 | 11.0-12.2 | | |
| H22 | 11.5 | | | | | |
| H23 | 12.0 | | | | | |
| H24 | 12.5 | $H_{24-26}$ | HP9 | 12.3-13.5 | | |
| H25 | 13.0 | | | | | |
| H26 | 13.5 | | | | | |

*SUBPOPULATION GROUPINGS AS GUIDED BY DIABETES RISK ASSOCIATIONS IN MESA.

HMP brackets: H9-H14 OR H9-H15 OR H9-H17

FIG. 4

TABLE: CHARACTERISTICS OF THE MESA STUDY POPULATION (n=3450)

| Characteristic | Mean (SD) | Characteristic | Mean (SD) |
|---|---|---|---|
| Age (years) | 60.1 (9.6) | Fasting glucose (mg/dL) | 89.0 (10.4) |
| Male Gender (%) | 47.6 | Impaired fasting glucose (%) | 14.6 |
| Race/Ethnicity (%) | | Total cholesterol (mg/dL) | 195 (35) |
| Caucasians | 44.8 | Triglycerides (mg/dL) | 128 (74) |
| African Americans | 22.1 | HDL cholesterol (mg/dL) | 51.7 (14.9) |
| Hispanics | 20.6 | Valine (µmol/L) | 242 (41) |
| Chinese | 12.5 | GlycA (µmol/L) | 323 (51) |
| BMI (kg/m²) | 28.0 (5.3) | Short-term DM converters | 181 |
| Hypertension (%) | 37.4 | Long-term DM converters | 286 |

FIG. 7

PARAMETERS CONTRIBUTING TO eLP-IR MULTIMARKER OF INSULIN RESISTANCE

| Model | 1-SD | Model R² | Δ lnHOMA (SE) per 1-SD | p |
|---|---|---|---|---|
| Model 1 |  |  |  |  |
| age, sex, race, glucose |  | 0.3285 | --- | --- |
| Model 2 |  |  |  |  |
| Model 1 + 5 eLP-IR parameters |  | 0.5050 | --- | --- |
| LP-IR | 23.6 |  | 0.221 (0.009) | <0.0001 |
| Valine (µmol/L) | 41.2 |  | 0.070 (0.008) | <0.0001 |
| Med VLDL-P (nmol/L) | 21.4 |  | -0.056 (0.008) | <0.0001 |
| Med HDL-P (µmol/L) | 6.5 |  | -0.071 (0.007) | <0.0001 |
| GlycA (µmol/L) | 51.1 |  | 0.043 (0.007) | <0.0001 |
| Model 3 |  |  |  |  |
| Model 1 + eLP-IR |  | 0.5050 |  |  |
| eLP-IR | 0.26 |  | 0.261 (0.007) | <0.0001 |

FROM MULTIPLE LINEAR REGRESSION IN MESA (n=3446) WITH INSULIN RESISTANCE (lnHOMA-IR) AS DEPENDENT VARIABLE. STRENGTHS OF ASSOCIATION OF EACH VARIABLE WITH INSULIN RESISTANCE ARE GIVEN AS THE DIFFERENCE IN ln(HOMA-IR) PER 1-SD INCREMENT. eLP-IR WAS DERIVED AS FOLLOWS USING BETA-COEFFICIENTS FROM MODEL 2:

$$eLP\text{-}IR = (0.00935)(LP\text{-}IR) + (0.001687)(VALINE) - (0.002594)(VLDL\text{-}P_{MED}) - (0.01096)(HDL\text{-}P_{MED}) + (0.000848)(GlycA)$$

© 2014 LIPOSCIENCE, INC.

FIG. 12

PARAMETERS CONTRIBUTING TO SDRF (SHORT-TERM DIABETES RISK FACTOR) SCORE

| Logistic Regression Model | Short-term Diabetes Conversion Diabetes at Visits 2 or 3 (mean 1.8 yrs; n=181/3450) | | | | Long-term Diabetes Conversion Diabetes at Visits 4 or 5 (mean 7.8 yrs; n=286/3269) | | | |
|---|---|---|---|---|---|---|---|---|
| | LR$\chi^2$ | AUC | OR | p | LR$\chi^2$ | AUC | OR | p |
| Model 1 | | | | | | | | |
| age, sex, race, glucose | 523.8 | 0.896 | — | — | 273.9 | 0.763 | — | — |
| Model 2 | | | | | | | | |
| Model 1 + HOMA-IR | | | | | | | | |
| HOMA-IR | 538.1 | 0.904 | 1.38 | 0.003 | 314.1 | 0.793 | 1.63 | <0.0001 |
| Model 3 | | | | | | | | |
| Model 1 + eLP-IR | | | | | | | | |
| eLP-IR | 555.4 | 0.911 | 1.85 | <0.0001 | 325.1 | 0.795 | 1.73 | <0.0001 |
| Model 4 | | | | | | | | |
| Model 3 + SDRF components | 567.9 | 0.914 | — | — | 325.9 | 0.796 | — | — |
| eLP-IR | | | 1.76 | <0.0001 | | | 1.68 | <0.0001 |
| HDL-P$_{MED}$ | | | (−) | 0.0004 | | | (+) | 0.61 |
| GlycA | | | (−) | 0.009 | | | (+) | 0.45 |
| HDL-P$_{MED}$ × GlycA | | | (+) | 0.0006 | | | (−) | 0.55 |
| Model 5 | | | | | | | | |
| Model 1 + eLP-IR + SDRF | 567.9 | 0.914 | — | — | 325.2 | 0.795 | — | — |
| eLP-IR | | | 1.77 | <0.0001 | | | 1.74 | <0.0001 |
| SDRF | | | 1.50 | 0.0004 | | | 0.98 | 0.76 |

FROM LOGISTIC REGRESSION IN MESA WITH SHORT-TERM (n=181/3450) OR LONG-TERM (n=286/3269) DIABETES CONVERSION AS DEPENDENT VARIABLE. STRENGTHS OF ASSOCIATION ARE GIVEN BY THE ODDS RATIO (OR) PER 1-SD INCREMENT. SDRF WAS DERIVED AS FOLLOWS USING BETA-COEFFICIENTS FROM MODEL 4 FOR SHORT-TERM DIABETES CONVERSION:

$$\text{SDRF} = -(0.352)(\text{HDL-P}_{MED}) - (0.0108)(\text{GlycA}) + (0.000969)(\text{GlycA} \times \text{HDL-P}_{MED})$$

© 2014 LIPOSCIENCE, INC.

FIG. 13 eLP-IR AND SDRF PREDICT 5-YEAR DIABETES CONVERSION IN IRAS (INSULIN RESISTANCE ATHEROSCLEROSIS STUDY)

Conversion to Diabetes During 5.2-Year Follow-up in IRAS (n=134/976)

| Model | LR$\chi^2$ | AUC | OR | p |
|---|---|---|---|---|
| Model 1 age, sex, race, glucose | 92.6 | 0.749 | 2.49 | <0.0001 |
| Model 2 Model 1 + Si | 100.0 | 0.765 | -- | -- |
| Si | | | 0.62 | <0.0001 |
| Model 3 Model 1 + LP-IR | 119.9 | 0.774 | -- | -- |
| LP-IR | | | 1.82 | <0.0001 |
| Model 4 Model 1 + eLP-IR | 124.2 | 0.780 | -- | -- |
| eLP-IR | | | 1.91 | <0.0001 |
| Model 5 Model 4 + SDRF | 129.3 | 0.787 | -- | -- |
| eLP-IR | | | 1.90 | <0.0001 |
| SDRF | | | 1.27 | 0.02 |

FROM LOGISTIC REGRESSION IN IRAS WITH 5-YEAR DIABETES CONVERSION AS DEPENDENT VARIABLE. RELATIVE PREDICTIVE VALUES OF THE 5 REGRESSION MODELS ARE GIVEN BY THE LIKELIHOOD RATIO (LR) $\chi^2$ STATISTIC AND AREA UNDER THE ROC CURVE (AUC). STRENGTHS OF ASSOCIATION OF THE INDICATED VARIABLES ARE GIVEN BY THE ODDS RATIO (OR) PER 1-SD INCREMENT. $S_I$ IS INSULIN SENSITIVITY MEASURED BY FREQUENTLY SAMPLED INTRAVENOUS GLUCOSE TOLERANCE TESTING.

© 2014 LIPOSCIENCE, INC.

*FIG. 14*

MEANING OF HDL-P$_{MED}$ x GlycA INTERACTION IN IRAS

RATES OF 5-Yr DIABETES CONVERSION IN IRAS BY TERTILE OF GlycA AND HDL-P$_{MED}$ TERTILE

| | GlycA Tertile | | |
|---|---|---|---|
| HDL-P$_{MED}$ Tertile | Low | Intermed | High |
| Low | 10.1% n=109 | 13.3% n=98 | 12.9% n=70 |
| Intermed | 7.1% n=99 | 7.7% n=91 | 11.8% n=93 |
| High | 2.3% n=86 | 9.3% n=97 | 17.8% n=107 |

DIABETES CONVERSION RATES BY TERTILE OF HDL-P$_{MED}$ AND GlycA IN IRAS PARTICIPANTS WITH FASTING GLUCOSE ≤110 mg/dL (n=88/850).
© 2014 LIPOSCIENCE, INC.

FIG. 15

LIPOSCIENCE

LIPOSCIENCE, INC.
2500 SUMMER BOULEVARD
RALEIGH, NC 27616
877-547-6837
WWW.LIPOSCIENCE.COM

| PAGE 1 OF 1 | PATIENT NAME | SEX | AGE | CLINICIAN |
|---|---|---|---|---|
| | DUPLICATE, TESTING1 | F | 33 | 5299 |

| PATIENT ID | BIRTH DATE | ACCESSION NUMBER |
|---|---|---|
| 5645 | NOT GIVEN | T0000651 |

CLIENT NAME AND ADDRESS
TEST RECORD        CHIPEDWIN/
2222 CAPITOL BLVD
SUITE 140
RALEIGH, NC
PHONE: (919)256-1111  FAX: (919)256-1221

| DATE COLLECTED | DATE RECEIVED | REPORT DATE AND TIME | REQUISITION NUMBER | FASTING STATUS |
|---|---|---|---|---|
| | | | TESTREQ1234 | FASTING |

NMR DIABETES RISK PROFILE® TEST

DIABETES RISK INDEX: 7.5

LOW RISK ←————————————— 7.5 —————→ HIGH RISK
1   2   3   4   5   6   7   8   9   10

THE DIABETES RISK INDEX (DRI) IS DERIVED FROM SEVERAL NONGLYCEMIC MARKERS OF INSULIN RESISTANCE[1], INFLAMMATION, AND PANCREAS BETA-CELL FUNCTION. THESE ARE THE MAJOR METABOLIC DRIVERS OF THE DEVELOPMENT OF TYPE 2 DIABETES, IRRESPECTIVE OF GLUCOSE LEVEL.

DIABETES RISK INTERPRETATION WITH GLUCOSE RESULTS

GLUCOSE LEVELS mg/dL — ESTIMATED 5-YEAR PROBABILITY OF PROGRESSION TO TYPE 2 DIABETES (%)

NORMAL: 70-99

| | LOW RISK | MODERATE RISK | HIGH RISK | VERY HIGH RISK |
|---|---|---|---|---|
| 95-99 | 1 | DRI | 10 | |
| [103] 100-110 | 1 | DRI | 7.5 | 10 |

5%  10%  15%  20%  25%  30%  40%  85%

5 YEAR RISK CATEGORY: VERY HIGH — YOU HAVE AN ESTIMATED 27% PROBABILITY OF PROGRESSING TO TYPE 2 DIABETES WITHIN 5 YEARS.

CARDIOVASCULAR IMPLICATIONS OF DIABETES RISK
PATIENTS WITH AN ELEVATED DRI ARE LIKELY TO HAVE HIGHER LDL PARTICLE NUMBER (LDL-P), AND INCREASED LDL-RELATED CARDIOVASCULAR RISK, DESPITE NORMAL OR DECREASED LDL CHOLESTEROL (LDL-C) VALUES. CONSIDER MEASURING LDL-P BY THE NMR LIPOPROFILE® TEST TO AID IN THE MANAGEMENT OF LDL-RELATED CARDIOVASCULAR RISK.

HISTORICAL REPORTING
STR (β CELL DYSFUNCTION)
6/10/13  STR: 9  FPG: 103
1   2   3   4   5   6   7   8   9   10
1/15/14  STR: 7.5  FPG: 103

ADDITIONAL INFORMATION
GlycA [400] μmol/L    VALINE [260] μmol/L
REF. RANGE: 243-498    REF. RANGE: 150-333

GlycA, A MARKER OF SYSTEMIC INFLAMMATION, AND VALINE, A BRANCHED-CHAIN AMINO-ACID, HAVE STRONG CLINICAL ASSOCIATIONS WITH PROGRESSION TO TYPE 2 DIABETES THESE LABORATORY ASSAYS, VALIDATED BY LIPOSCIENCE, HAVE NOT BEEN CLEARED BY THE US FOOD AND DRUG ADMINISTRATION. THE CLINICAL UTILITY OF THESE LABORATORY VALUES HAVE NOT BEEN FULLY ESTABLISHED. © 2015 LIPOSCIENCE, INC. ALL RIGHTS RESERVED

*FIG. 17*

LIPOSCIENCE

LIPOSCIENCE, INC.
2500 SUMMER BOULEVARD
RALEIGH, NC 27616
877-547-6837
WWW.LIPOSCIENCE.COM

| PAGE 1 OF 1 | PATIENT NAME | SEX | AGE | CLINICIAN |
|---|---|---|---|---|
| | DUPLICATE, TESTING1 | F | 33 | 5299 |

| PATIENT ID | BIRTH DATE | ACCESSION NUMBER |
|---|---|---|
| 5645 | NOT GIVEN | T0000651 |

CLIENT NAME AND ADDRESS
TEST RECORD    CHIPEDWIN/
2222 CAPITOL BLVD
SUITE 140
RALEIGH, NC
PHONE: (919)256-1111  FAX: (919)256-1221

| DATE COLLECTED | DATE RECEIVED | REPORT DATE AND TIME | REQUISITION NUMBER | FASTING STATUS |
|---|---|---|---|---|
| | | | TESTREQ1234 | FASTING |

NMR DIABETES RISK PROFILE® TEST
DIABETES RISK INDEX: 7.5

LOW RISK ———————————————————— HIGH RISK
1  2  3  4  5  6  7  8  9  10

THE DIABETES RISK INDEX (DRI) IS DERIVED FROM SEVERAL NONGLYCEMIC MARKERS OF INSULIN RESISTANCE[1], INFLAMMATION, AND PANCREAS BETA-CELL FUNCTION. THESE ARE THE MAJOR METATABOLIC DRIVERS OF THE DEVELOPMENT OF TYPE 2 DIABETES, IRRESPECTIVE OF GLUCOSE LEVEL.

DIABETES RISK INTERPRETATION WITH GLUCOSE RESULTS
GLUCOSE LEVELS mg/dL  ESTIMATED 5-YEAR PROBABILITY OF PROGRESSION TO TYPE 2 DIABETES (%)
NORMAL: 70-99

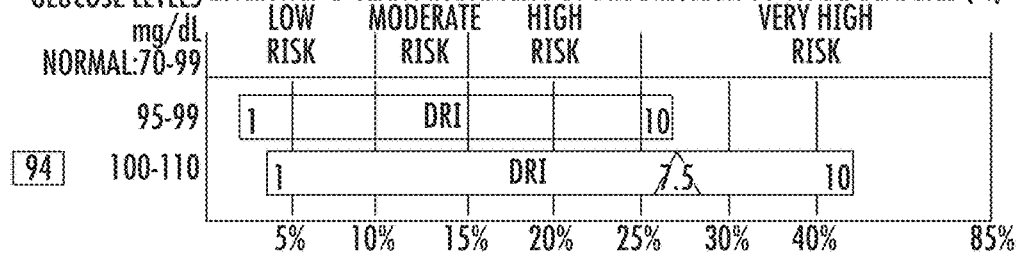

| | LOW RISK | MODERATE RISK | HIGH RISK | VERY HIGH RISK |
|---|---|---|---|---|
| 95-99 | 1 | DRI | 10 | |
| [94] 100-110 | 1 | DRI | 7.5 | 10 |

5%  10%  15%  20%  25%  30%  40%  85%

5 YEAR RISK CATEGORY: LOW    YOUR FASTING GLUCOSE IS BELOW 95 mg/dL, AND YOUR PROBABILITY OF PROGRESSING TO TYPE 2 DIABETES WITHIN 5 YEARS IS < 10%.

CARDIOVASCULAR IMPLICATIONS OF DIABETES RISK
PATIENTS WITH AN ELEVATED DRI ARE LIKELY TO HAVE HIGHER LDL PARTICLE NUMBER (LDL-P), AND INCREASED LDL-RELATED CARDIOVASCULAR RISK, DESPITE NORMAL OR DECREASED LDL CHOLESTEROL (LDL-C) VALUES. CONSIDER MEASURING LDL-P BY THE NMR LIPOPROFILE® TEST TO AID IN THE MANAGEMENT OF LDL-RELATED CARDIOVASCULAR RISK.

HISTORICAL REPORTING
6/10/13 DRI: 9 FPG:94

DRI

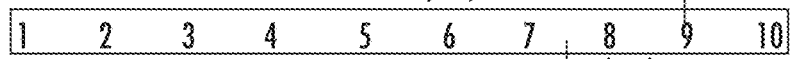

1  2  3  4  5  6  7  8  9  10
▷1/15/14 DRI: 7.5 FPG:94

ADDITIONAL INFORMATION
GlycA [400] μmol/L    VALINE [260] μmol/L
REF. RANGE: 243-498   REF. RANGE: 150-333

GlycA, A MARKER OF SYSTEMIC INFLAMMATION, AND VALINE, A BRANCHED-CHAIN AMINO-ACID, HAVE STRONG CLINICAL ASSOCIATIONS WITH PROGRESSION TO TYPE 2 DIABETES THESE LABORATORY ASSAYS, VALIDATED BY LIPOSCIENCE, HAVE NOT BEEN CLEARED BY THE US FOOD AND DRUG ADMINISTRATION. THE CLINICAL UTILITY OF THESE LABORATORY VALUES HAVE NOT BEEN FULLY ESTABLISHED.   © 2015 LIPOSCIENCE, INC. ALL RIGHTS RESERVED

*FIG. 20C*

MULTIPLE-MARKER RISK PARAMETERS PREDICTIVE OF CONVERSION TO DIABETES

RELATED APPLICATIONS

This application claims the benefit of and priority to U.S. Provisional Patent Application Ser. No. 61/923,855, filed Jan. 6, 2014, the contents of which are hereby incorporated by reference as if recited in full herein. The application is also a continuation-in-part of PCT/US2013/044679, filed Jun. 7, 2013, which is a continuation-in-part of U.S. Ser. No. 13/830,784 and claims the benefit of priority of U.S. Provisional Application Ser. No. 61/657,315, filed Jun. 8, 2012, U.S. Provisional Application Ser. No. 61/711,471, filed Oct. 9, 2012 and U.S. Provisional Application Ser. No. 61/739,305, filed Dec. 19, 2012, the contents of which are hereby incorporated by reference as if recited in full herein.

RESERVATION OF COPYRIGHT

A portion of the disclosure of this patent document contains material which is subject to copyright protection. The copyright owner, LipoScience, Inc., has no objection to the reproduction by anyone of the patent document or the patent disclosure, as it appears in the Patent and Trademark Office patent file or records, but otherwise reserves all copyright rights whatsoever.

FIELD OF THE INVENTION

The present invention relates generally to analysis of in vitro biosamples.

BACKGROUND OF THE INVENTION

Type 2 diabetes mellitus (T2DM or "diabetes") is one of the most costly and burdensome chronic diseases in the U.S. and other countries. The defining feature of T2DM is hyperglycemia, a reflection of impaired carbohydrate (glucose) utilization resulting from a defective or deficient insulin secretory response. T2DM is a late manifestation of metabolic derangements that begin many years earlier. Its cause is believed to be a progressive increase in insulin resistance coupled with deteriorating β-cell function. So long as the pancreatic β-cells are able to secrete enough insulin to compensate for the progressive resistance of target tissues to insulin's hypoglycemic effects, the patient is able to maintain normal fasting glucose levels. Hyperglycemia and the transition to T2DM occur as a consequence of progressive β-cell dysfunction which leads to failure to maintain hypersecretion of insulin in the face of increasing insulin resistance.

Type 2 diabetes has been traditionally diagnosed by the detection of elevated levels of glucose (sugar) in the blood (hyperglycemia). While hyperglycemia defines diabetes, it is a very late stage development in the chain of events that lead from insulin resistance to full-blown diabetes. Accordingly, it would be desirable to have a way of identifying whether or not a subject is at risk for developing Type 2 diabetes (i.e., is predisposed to the condition) prior to the development of the classic symptoms, such as hyperglycemia. Earlier detection of indicators of the disease (e.g., detection before glucose levels are elevated enough to be considered hyperglycemia) may lead to more effective treatment of the disease, if not actual prevention of the onset of the disease.

The most direct and accurate methods for assessing insulin resistance are laborious and time-consuming, and thus impractical for clinical application. The "gold standard" among these research methods is the hyperinsulinemic euglycemic clamp, which quantifies the maximal glucose disposal rate (GDR, inversely proportional to insulin resistance) during the clamp. Another arduous research method which is somewhat less reproducible (CV 14-30%) is the frequently sampled intravenous glucose tolerance test (IVGTT) with minimal model analysis, which measures insulin sensitivity ($S_i$), the inverse of insulin resistance.

Risk of progression to Type 2 diabetes is currently assessed primarily by fasting glucose, with concentrations 100-125 mg/dL defining a high-risk "pre-diabetes" condition and for which T2DM is currently defined in patients having fasting plasma glucose levels at 126 mg/dL and above. However, the actual risk of individual patients with pre-diabetes (those at greatest risk of developing T2DM in the near future) varies widely.

NMR spectroscopy has been used to concurrently measure low density lipoproteins (LDL), high density lipoproteins (HDL), and very low density lipoproteins (VLDL), as LDL, HDL and VLDL particle subclasses from in vitro blood plasma or serum samples. See, U.S. Pat. Nos. 4,933,844 and 6,617,167, the contents of which are hereby incorporated by reference as if recited in full herein. U.S. Pat. No. 6,518,069 to Otvos et al. describes NMR derived measurements of glucose and/or certain lipoprotein values to assess a patient's risk of developing T2DM.

Generally stated, to evaluate the lipoproteins in a blood plasma and/or serum sample, the amplitudes of a plurality of NMR spectroscopy derived signals within a chemical shift region of NMR spectra are derived by deconvolution of the composite methyl signal envelope to yield subclass concentrations. The subclasses are represented by many (typically over 60) discrete contributing subclass signals associated with NMR frequency and lipoprotein diameter. The NMR evaluations can interrogate the NMR signals to produce concentrations of different subpopulations, typically seventy-three discrete subpopulations, 27 for VLDL, 20 for LDL and 26 for HDL. These sub-populations can be further characterized as associated with a particular size range within the VLDL, LDL or HDL subclasses.

An advanced lipoprotein test panel, such as the LIPO-PROFILE® lipoprotein test, available from LipoScience, Raleigh, N.C., has typically included a total high density lipoprotein particle (HDL-P) measurement (e.g., HDL-P number) that sums the concentration of all the HDL subclasses and a total low density lipoprotein particle (LDL-P) measurement that sums the concentration of all the LDL subclasses (e.g., LDL-P number). The LDL-P and HDL-P numbers represent the concentration of those respective particles in concentration units such as nmol/L. LipoScience has also developed a lipoprotein-based insulin resistance and sensitivity index (the "LP-IR™" index) as described in U.S. Pat. No. 8,386,187, the contents of which are hereby incorporated by reference as if recited in full herein.

FIG. 1A illustrates a timeline over which insulin resistance and insulin production change before onset of T2DM, with β-cell dysfunction occurring during the progression. Glucose may remain relatively stable before rapidly increasing during progression to T2DM. See, e.g., Mason et al., Diabetes 2007; 56: 2054-6. FIG. 1B illustrates various glucose ranges and a continuum of T2DM progression during which diabetic complications can occur. Many with glucose in the 100-110 mg/dL range do not progress to T2DM and others with "normal" glucose in the range of 90-99 mg/dL, for example, may develop diabetes in less than five years. Currently the risk of diabetes progression is primarily evaluated by glucose measures that are the response to, not the cause of, worsening glucose metabolism. There is an unmet diagnostic need for tests that can better distinguish between those that will progress to diabetes from those that will not. See, AACE Prediabetes Consensus Statement, Endocr Pract. 2008; 14 (No. 7) 941.

There remains a need for evaluations that can predict or assess a person's risk of developing type 2 diabetes before the onset of the disease and/or to identify those individuals at risk of progression early so that interventions may be used to delay progression and/or treat cardiovascular risk.

SUMMARY

Embodiments of the invention provide multimarkers of (i) insulin resistance ("IR"), (e.g, eLP-IR) and (ii) short-term diabetes risk factors (SDRF) of fasting plasma biosamples that can assess diabetes risk at any level of glycemia.

Embodiments of the invention provide risk assessments of a subject's risk of developing type-2 diabetes in the future using multi-parameter (multi-variate) risk progression models, one model for SDRF associated with short term risk ("STR") (e.g., less than 3 years, such as within 6 months, 1 year, 2 year or 3 years, post test) and another for IR which can be an important risk parameter for both STR and longer term risk ("LTR") (e.g., greater than 3 years, such as 3.5 years, 4 years, 5 years or between 5-10 years, post test).

The SDRF can be provided as a score. The SDRF score is positively associated with short term risk and therefore is thought to be inversely related to beta cell function or positively related to pancreatic beta cell dysfunction.

The IR score can be identified using an "eLP-IR" (extended lipoprotein insulin resistance) score.

The STR model (assessed with logistic regression). The IR model can be assessed with linear regression models for either or both HOMA-IR or Si (insulin sensitivity, as assessed by frequently sampled intravenous glucose tolerance testing) based on at least one study population.

Embodiments of the invention may use the multi-parameter diabetes risk parameters as inputs to a diabetes risk model to generate a diabetes risk index (DRI) score associated with risk of conversion within a defined timeline, typically five years.

Coefficients for the risk models can be defined by logistic regression for respective short term and longer term diabetes conversion (per the IR model) to generate an equation that can combine the various marker inputs.

The SDRF parameter (for STR) and the IR parameter can be provided as a numerical score or value in a defined range, lower numbers for lower risk and higher values for higher risk. In some embodiments, the SDRF and IR scores can be combined to provide a diabetes risk index ("DRI") score.

Embodiments of the invention may provide a logistic regression model with components from both the SDRF and IR models for a DRI score or a "diabetes risk index" that typically is associated with a timeline of between 3-7 years, e.g., about 5 years, post-test.

Embodiments of the invention can generate an STR evaluation that can be used to identify at-risk patients that may benefit from therapies for improving or stabilizing beta-cell function and/or improve a patient's ability to produce insulin. It is contemplated that a non-limiting example of such a therapy can be reconstituted HDL infusion therapy that has been used for post-myocardial infarction patients.

Embodiments of the invention can provide STR scores for drug therapy, drug discovery and/or clinical trials. The STR score can be used as a marker to identify a dysfunction and/or a change in beta-cell function.

The STR score can be a relative score or an absolute score relative to a defined population. The STR score can be used with a baseline STR score and a subsequent STR score for a subject where a change reflects a change from an administered therapy or drug discovery program.

The STR, IR and/or DRI scores can be generated before, during and/or after administration of a drug therapy to identify a change in respective scores for a subject and therefore identify beneficial or negative change from the drug therapy.

The SDRF and/or STR score can be used for evaluating therapies or drugs that may improve or stabilize beta-cell function and/or the ability to produce insulin or for evaluating undesired side-effects of drugs.

The risk assessments can generate respective STR, IR, and DRI scores that stratify risk beyond glucose measurements alone and may be decoupled from glucose measurements.

The DRI score, where used, may be based on risk prediction models of about a 5 year risk of conversion using some or all components from both the SDRF and IR risk prediction models, which may be weighted using different defined weighting factors to generate the DRI score. The risk assessments can consider glucose measurements. Where used, a glucose measurement can help establish a timeline of conversion to type 2 diabetes and/or be used in evaluation of risk. The diabetes risk index scores can be used without glucose information and may reflect risk over both a short term and a longer term associated with underlying metabolic issues.

The multi-variate models can be used for assessing patients for or during clinical trials, during a therapy or therapies, for drug development, for drug therapy selection or indication for a subject, and/or to identify or monitor anti-obesity drugs or other drug therapy candidates.

The short term multi-variate model can include NMR measurements of GlycA, a lipoprotein component (HMP) associated with concentration of a defined subpopulation of high density lipoprotein (HDL) particles, and an interaction parameter of the measurement of GlycA multiplied by HMP (the concentration of a defined subpopulation of high density lipoprotein (HDL) particles), HMP×GlycA.

While GlycA may be a preferred inflammation marker, other inflammation markers may be used including, for example, fibrinogen, haptoglobin, alpha-1-acid glycoprotein, CRP (C-reactive protein), hs)CRP (high sensitivity CRP), or IL-L (interleukin-6).

The HDL subpopulation can include only medium HDL particle subclasses (HMP). Medium HDL-P refers to a sub-population of HDL particles that excludes small and large HDL particle subclasses and the exact size range may vary between measurement methodologies and study populations which maximize risk of diabetes using a risk model (typically a logistic regression model of at least one defined study population), either or both in the short term or a risk model based on IR for a longer term.

By way of example only, the medium HDL-P may include only HDL particles with diameters between about 8.3 nm (average) to an upper value of 9.4 nm (average), or 10.0 nm (average) or 10.2 nm (average).

The SDRF and/or STR risk model can include components that are markers of impaired insulin secretion and/or pancreatic beta-cell dysfunction.

The DRI risk model can include components that are markers of insulin resistance as well as the SDRF markers or the SDRF score.

The IR multi-variate model can include at least one defined lipoprotein component and at least one defined branched chain amino acid. Optionally, the model may include at least one inflammatory biomarker. The longer term (IR) multi-variate model can include Valine, and a plurality of lipoprotein components (e.g., subclasses) derived from the same NMR spectrum. The plurality of lipoprotein components can include LP-IR and VMP (the concentration of a defined subpopulation of very low density lipoprotein particles, the medium VLDL subclass particle number or "medium VLDL-P").

The term "medium VLDL particles" or "VMP" refers to a concentration of particles with diameters/sizes between 35-60 nm (average).

The DRI risk model can include components from the SDRF and IR models, typically three from each including HMP, GlycA, HMP×GlycA from the STR model and LP-IR, Valine and med-VLDL-P from the IR model.

Embodiments of the invention include methods, circuits, NMR spectrometers or NMR analyzers, and processors that evaluate a future risk of developing diabetes and/or risk stratification for those having normal glucose or slightly elevated glucose by evaluating NMR spectra of an in vitro blood plasma or serum patient sample using defined short term and longer term multi-component risk progression models.

In some embodiments, the STR and IR scores can be weighted to generate a DRI score in a defined numerical range. In some embodiments, the IR score can be weighted to account for a greater contribution that IR makes to risk over a 5-year (or other longer term conversion time) relative to SDRF.

Embodiments of the invention are directed to methods of evaluating a subject's risk of developing type 2 diabetes and/or having pancreatic beta cell impairment and/or dysfunction. The methods include: programmatically calculating a short term diabetes risk factor (SDRF) score of a subject using a defined mathematical model of risk of developing type 2 diabetes. The defined mathematical model includes a concentration measurement of a defined high density lipoprotein particle (HDL-P) subpopulation, a concentration measurement of at least one inflammatory marker and a concentration measurement of at least one interaction parameter as components of the model which are mathematically combined with respective defined coefficients to generate the calculated SDRF score. The subject is at risk of converting to type 2 diabetes mellitus within 3 years and/or is at risk of beta cell dysfunction when the SDRF score is at a third tertile value or greater value of a population norm.

The defined HDL-P subpopulation can be medium HDL-P.

The inflammatory marker can be GlycA. The interaction parameter can be GlycA multiplied by the concentration of medium HDL-P. The subject is at risk of beta cell dysfunction when medium HDL-P and Glyc A values are in a third tertile values of the population norm.

The method can include programmatically calculating an insulin resistance (IR) score of the subject using a defined mathematical model of insulin resistance.

The defined mathematical model of insulin resistance for the IR score can include a plurality of components including a concentration measurement of a defined HDL-P subpopulation, which may be the concentration measurement of the defined HDL-P subpopulation used to calculate the SDRF score, the measurement of the inflammatory marker, a measurement of a defined subpopulation of VLDL-P (very low density lipoprotein/chylomicron particle subclasses), an IR index with a range of between 0-100, the range representing from low to high, insulin sensitivity to insulin resistance, and a measurement of a branched chain amino acid (BCAA), obtained from the at least one in vitro biosample of the subject.

The components of the defined mathematical model of IR can be mathematically combined to generate the IR score.

The measurement of the defined sub-population of VLDL-P can be a concentration of medium VLDL-P, and wherein the BCAA is Valine.

The method can include programmatically calculating a diabetes risk score by combining the SDRF score and the IR score.

The coefficients of the SDRF and IR scores can be derived from a logistic regression model that includes SDRF and IR to predict actual 5 year conversion to diabetes using at least one defined population study to thereby generate a DRI score with a risk of conversion within 5 years irrespective of a glucose value of the subject.

The method can include evaluating a measured glucose and/or HbA1c value of the subject and electronically providing a report with a 5 year risk of conversion to Type 2 diabetes risk estimate based on the glucose measurement and the DRI score.

The SDRF score can be calculated using the following equation: SDRF score=−(A) (HDL-$P_{MED}$)−(B) (GlycA)+ (C) (GlycA×HDL-$P_{MED}$), where A, B and C can be defined beta coefficients from a logistic regression model for short term conversion to diabetes as the defined mathematical model of risk of developing type 2 diabetes. GlycA can be the inflammatory marker, HDL-$P_{MED}$ is a medium size HDL-P subpopulation, and GlycA×HDL-$P_{MED}$ can be the interaction parameter.

The IR score can be an eLP-IR score and is calculated using the following equation: eLP-IR=(A) (LP-IR)+(B)(Valine)−(C) (VLDL-$P_{MED}$)−(D)(HDL-$P_{MED}$)+(E)(GlycA). A, B, C, D and E can be defined beta coefficients from a linear regression model for insulin resistance. GlycA can be the inflammatory marker, HDL-$P_{MED}$ can be the concentration of a medium HDL-P subpopulation, VLDL-$P_{MED}$ can be a concentration of a medium VLDL-P subpopulation, valine can be a branched chain amino acid, and LP-IR can be a lipoprotein insulin resistance index calculated using six defined lipoprotein subclasses and has a numerical value in a range of 0-100 representing insulin sensitive to insulin resistance.

The method can also include at least one of: evaluating a drug therapy, evaluating a clinical trial, or evaluating candidates for drug discovery, using the SDRF score.

The method can include calculating a plurality of the SDRF scores over time from respective biosamples to thereby evaluate a change in SDRF score to identify a change in β-cell dysfunction.

The raw scores associated with the SDRF score can be between −6.4 and −1.6, wherein −4.1 can be associated with about a $25^{th}$ percentile and >−3.8 can be associated with about a $75^{th}$ percentile of the study population. Scores ≥−3.8 values can indicate an increased risk of beta cell dysfunction and/or early conversion to type 2 diabetes independent of glycemic value that can stratify risk of conversion to type 2 diabetes for subjects having a common glycemic measurement with different SDRF scores.

The SDRF score can be provided in a report in a defined numerical score range, with scores associated with a fourth quartile (4Q), fifth quintile (5Q) or $10^{th}$ decile of a population norm reflecting an increased risk of developing type 2 diabetes within 2 years and/or beta cell dysfunction and/or impairment relative to lower scores.

The HDL-P subpopulation can include only medium HDL particle subclasses with diameters between 8.3 nm to one of: 9.4 nm, 10.0 nm or 10.2 nm.

The method can include generating a DRI score using the following equation: DRI score=X(IR score)+Y(SDRF). X and Y can be coefficients defined by a logistic regression model for 5-year diabetes conversion in people with glucose <110 mg/dL using a defined study population, and wherein the DRI score is mathematically altered into a DRI score range using a plurality of equal subparts over a range of possible DRI raw scores.

The raw DRI scores may be between about −3.0 to about 1.8.

Embodiments of the invention can be directed to methods of identifying at-risk patients that may benefit from therapies for improving or stabilizing beta-cell function and/or improve a patient's ability to produce insulin. The methods can include electronically generating a short term risk score by combining measurements of defined lipoprotein and metabolite components of a biosample of a subject, wherein the components include a high density lipoprotein particle (HDL-P) subpopulation and an interaction parameter using the HDL-P subpopulation and an inflammatory marker.

Other embodiments are directed to methods of identifying subjects that are likely to benefit from a drug therapy such as reconstituted HDL infusion for improving pancreatic beta cell function and/or to inhibit Type 2 diabetes mellitus (T2DM). The methods can include generating a defined short term diabetes risk factor (SDRF) score using measurements of defined lipoprotein and metabolite components of a biosample of a subject. The components include a high density lipoprotein particle (HDL-P) subpopulation and an interaction parameter using the HDL-P subpopulation and an inflammatory marker; and identifying subjects that have an increased SDRF score relative to a defined population norm which indicates that the subject is likely to benefit from therapy to improve pancreatic beta cell function and/or inhibit T2DM.

The methods can be carried out using at least one processor.

All or some of the measurements of the biosample for the SDRF score can all be NMR derived measurements.

Other embodiments are directed to methods of evaluating a patient's risk of conversion to type 2 diabetes by:

(a) programmatically calculating a SDRF score using the following equation: SDRF score=−(A) (HDL-$P_{MED}$)−(B) (GlycA)+(C) (GlycA×HDL-$P_{MED}$), wherein A, B and C are defined beta coefficients from a logistic regression model for short term conversion to diabetes as the defined mathematical model of risk of developing type 2 diabetes, and wherein GlycA is an inflammatory marker, HDL-$P_{MED}$ is a medium size HDL-P subpopulation, and GlycA×HDL-$P_{MED}$ is an interaction parameter;

(b) programmatically calculating an eLP-IR score and using the following equation: eLP-IR=(A) (LP-IR)+(B)(Valine)−(C) (VLDL-$P_{MED}$)−(D)(HDL-$P_{MED}$)+(E)(GlycA), wherein A, B, C, D and E are defined beta coefficients from a linear regression model for insulin resistance, wherein GlycA is the inflammatory marker, HDL-$P_{MED}$ is the concentration of a medium HDL-P subpopulation, VLDL-$P_{MED}$ is a concentration of a medium VLDL-P subpopulation, valine is a branched chain amino acid, and LP-IR is a lipoprotein insulin resistance index calculated using six defined lipoprotein subclasses and has a numerical value in a range of 0-100 representing insulin sensitive to insulin resistance, and (c) programmatically generating a DRI raw score using the following equation: DRI raw score=X(eLP-IR)+Y (SDRF), wherein X and Y are coefficients defined by a logistic regression model for 5-year diabetes conversion in people with glucose <110 mg/dL using a defined study population, and wherein the DRI raw score is mathematically altered into a range of between 0-10 or 1-10 using a plurality of equal subparts over a range of possible DRI raw scores.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 4 is a chart of exemplary HDL subpopulation groupings for diabetes risk assessment based on associations (positive and negative) with incident diabetes according to embodiments of the present invention.

FIG. 7 is a table of the characteristics of the MESA study population (n=3450).

FIG. 12 is a chart of parameters contributing to the eLP-IR multimarker parameter of insulin resistance according to embodiments of the present invention.

FIG. 13 is a chart of parameters contributing to the SDRF multimarker parameter of short term risk according to embodiments of the present invention.

FIG. 14 is a chart illustrating the conversion to diabetes during 5.2 year follow-up in IRAS (n=134/976) which validates the model developed using MESA according to embodiments of the present invention.

FIG. 15 is a chart illustrating the actual rates (in percent) of 5-year conversion to diabetes within 9 subgroups of IRAS participants (all with fasting glucose less than or equal to 110 mg/dL) subdivided according to their levels (low, intermediate or high) of GlycA and medium HDL-P (HDL-$P_{MED}$) according to embodiments of the present invention. Among the noted 850 participants, 88 converted to diabetes.

FIG. 17 is an exemplary report which provides a measure of short term risk, e.g., a SDRF score, which may be monitored for change to assess β-cell function/dysfunction over time.

FIGS. 20A-20C illustrate exemplary patient reports with DRI scores associated with risk categories to predict a conversion to T2DM within a defined timeline such as 5 years according to embodiments of the present invention.

Figure 1A:
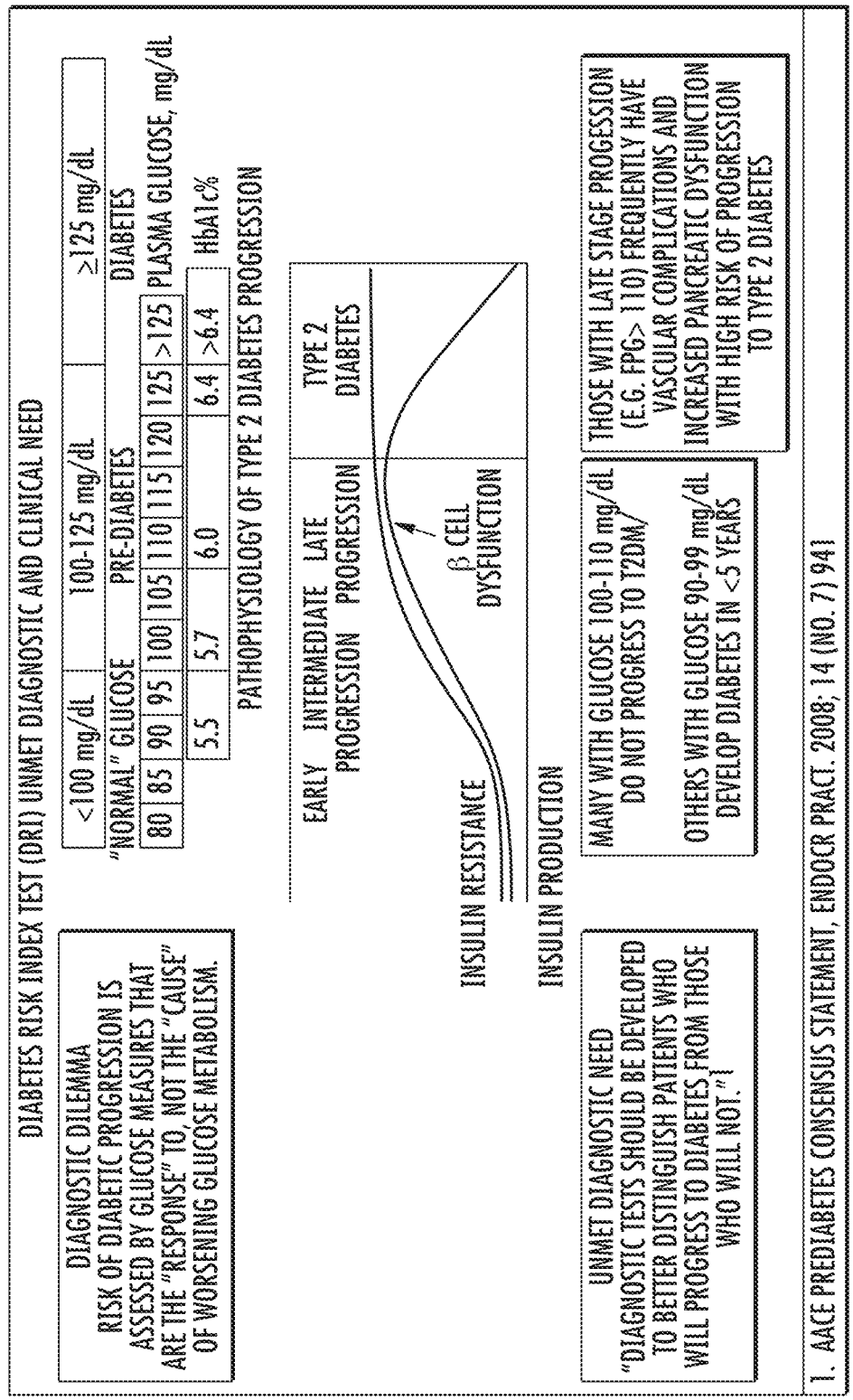
FIG. 1A is a chart illustrating pathophysiology of Type 2 diabetes progression.
Figure 1B:
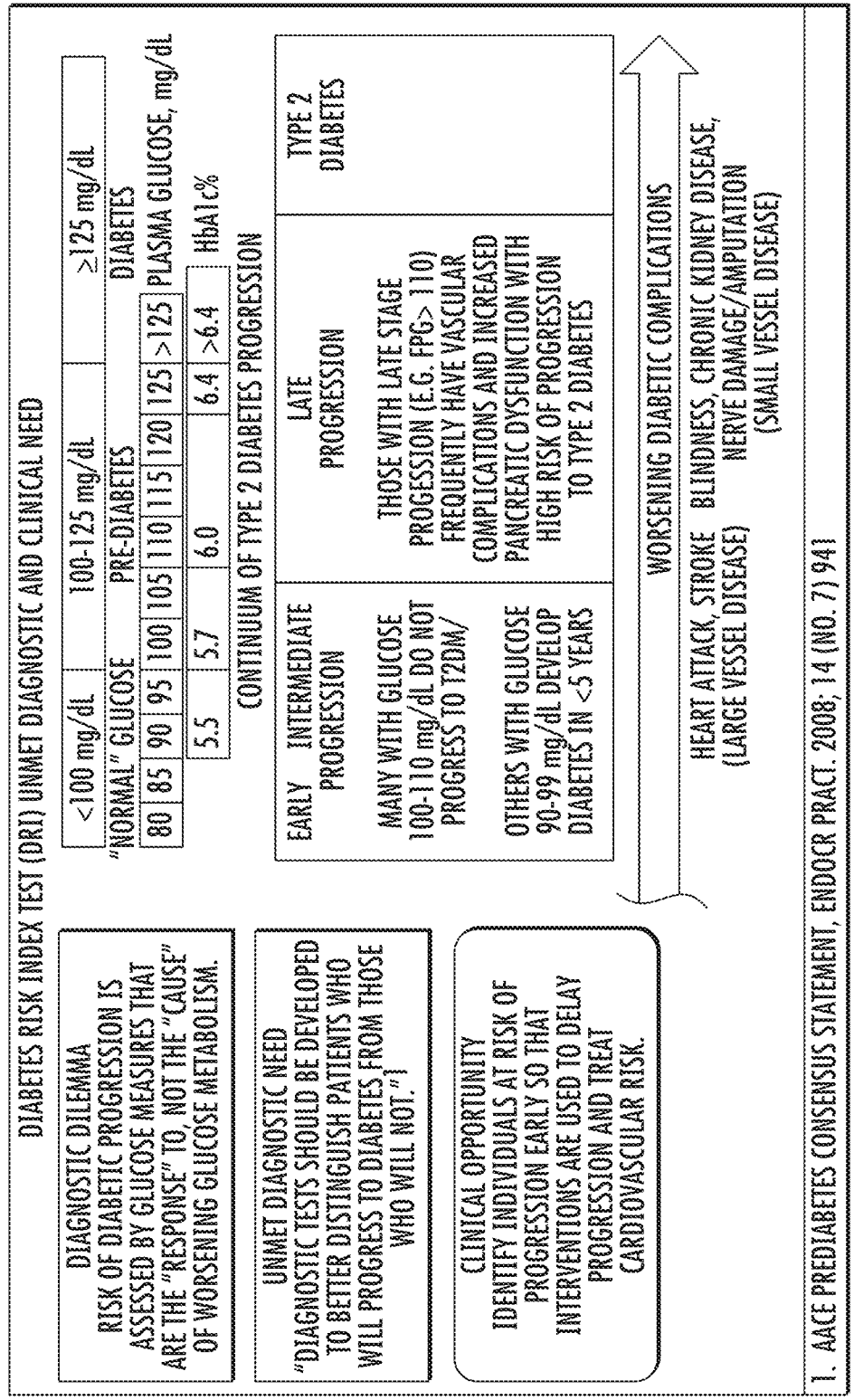
FIG. 1B is a chart illustrating a continuum of Type 2 diabetes progression with examples of worsening diabetic complications.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The term "Figure" is used interchangeably with the abbreviated versions "FIG." and "Fig." in the specification and figures.

Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Exemplary descriptions of components of risk progression models for diabetes risk indexes or scores are described in U.S. patent application Ser. No. 13/830,784, filed Mar. 14, 2013, and PCT/US2013/044679, filed Jun. 7, 2013, the contents of which are hereby incorporated by reference as if recited in full herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about" refers to +/−10% (mean or average) of a specified value or number.

The term "prediabetes" refers to a risk state for a patient or subject rather than a disease state. Thus, the term "prediabetes" refers to someone that has not been diagnosed with type 2 diabetes and, as currently defined by the American Diabetes Association, is associated with individuals that have a fasting plasma glucose level that is between 100 and 125 mg/dL, an oral glucose tolerance test level that is between 140-199 (mg/dL) or an A1C percent that is between 5.7 to 6.4 as represented in Table 1 below (the greater the level, the higher the risk of type 2 diabetes for each type of test).

TABLE 1

Blood Test Levels for Diabetes and Prediabetes

| | A1C (percent) | Fasting Plasma Glucose (mg/dL) | Oral Glucose Tolerance Test (mg/dL) |
|---|---|---|---|
| Diabetes | 6.5 or above | 126 or above | 200 or above |
| Prediabetes | 5.7 to 6.4 | 100 to 125 | 140 to 199 |
| Normal | About 5 | 99 or below | 139 or below |

Definitions:
mg = milligram,
dL = deciliter
For all three tests, within the prediabetes range, the higher the test result, the greater the risk of diabetes. See, American Diabetes Association. Standards of medical care in diabetes-2012. *Diabetes Care*. 2012: 35 (Supp 1): S12, table 2.

Embodiments of the invention may be particularly suitable to stratify risk for patients having the same or similar fasting glucose levels. Generally stated, it is contemplated that STR and IR scores, alone or combined into a DRI score, can be used to stratify risk for developing type 2 diabetes in the future alone or with FPG or other measure of glucose such as A1C (a non-fasting sample using hemoglobin A1C) or oral glucose tolerance measurements. One or more of a STR, IR or DRI diabetes risk score can be used to stratify type 2 diabetes risk for patients having the same glucose level, but different underlying metabolic situations.

The connection of SDRF with beta cell dysfunction is currently theoretical as no direct evidence that SDRF is actually associated with an objective measure of beta cell function (of which there aren't many and they aren't very good) has been established as of the filing date of this patent application. However, since SDRF contributes only to short but not long-term risk and is independent of IR, a connection to beta cell dysfunction is strongly implied, if currently only an inference.

Embodiments of the invention can provide a "cumulative" diabetes risk based on IR status and beta cell function, within a relatively short timeframe, typically 5 years. This risk is contributed to by insulin resistance (a necessary ingredient of diabetes risk no matter what the timeframe) and also by beta-cell dysfunction which is typically a late manifestation (influencing only relatively short-term conversion, typically within 2-3 years). So to assess risk of conversion to T2DM within 5 years, an assessment of both IR (e.g., eLP-IR) and beta-cell dysfunction (SDRF) can be used. The relative importance of the beta-cell part of the overall risk is greater if the timeframe of interest is shorter rather than longer, may be accounting for ~50% of the risk of 3-year conversion, ~30% of the risk of 5-year conversion, and <10% of the (cumulative) risk of 10-year conversion. Thus, embodiments of the invention can provide a new multimarker of 5-yr diabetes risk (a DRI score), which can combine the IR score and the SDRF score.

The longer the time period of interest, the more important that IR is to the risk of diabetes relative to SDRF. In some particular embodiments, one or both of these discrete scores can be "weighted" to correlate to the time frame of risk of interest. For example, the component parts of IR (e.g., eLP-IR) and SDRF can be weighted to have an increased value over the measured SDRF value to generate the DRI score. An equation to generate the DRI score is shown below.

$$\text{DRI score} = X(\text{IR}) + Y(\text{SDRF}) \quad \quad \text{EQUATION 1}$$

The DRI score can be a combination of the IR score and the SDRF score, and X and Y are defined coefficients where X>Y for LTR DRI evaluations. For example, X can be about 70% and Y can be about 30% for a 5 year risk of conversion timeline. X and Y can have other values. Table 2 includes examples of relative sets of weights for a 5 year risk of conversion to DRI score, which can have a maximum value of 1, 10 or 100, in some embodiments. It will be apparent, that the SDRF score can decrease in relevance to the DRI risk as the evaluation window/risk period increases.

TABLE 2

| IR AND SDRF WEIGHTS | | |
|---|---|---|
| DRI MAXIMUM | X % | Y % |
| 1, 10, 100 | 70 | 30 |
| 10 | 75 | 25 |
| 100 | 60 | 40 |

In some embodiments, the analysis can use diabetes conversion data from one or more study populations that has a 5 year (or other appropriate) observation period to run a logistic regression analysis that includes the following prediction variables: age, gender, race, fasting glucose, IR (e.g., eLP-IR or other IR measure) and SDRF. From this prediction model, the coefficients for IR and SDRF can be generated. Then DRI can be calculated as a defined coefficient (X) times IR (e.g., eLP-IR) plus a defined coefficient (Y) times SDRF, per equation (1). The longer the timeframe for the analysis, the more dominant IR scores will be relative to the SDRF scores. That is, the beta coefficients will provide the numbers for the associated statistical relationships which will not require any further weighting.

Embodiments of the invention provide clinical outputs of the DRI score as well as one or both of the two multi-marker parameters that can be combined to produce DRI score: the IR parameter (e.g., the eLP-IR score) which may be addressable by diet, exercise & weight loss and/or insulin sensitizing drugs, and the beta-cell dysfunction part, SDRF, which may be addressable potentially by drugs directed to this dysfunction. Another reason to measure and report an elevated SDRF is to alert the patient that diabetes is likely in their short-term future and therefore of more urgency to do something about (by weight loss at a minimum plus drugs).

Embodiments of the invention can employ STR scores to identify patients that may benefit from a drug therapy to improve or stabilize beta cell function.

Embodiments of the invention can employ STR scores to evaluate drug therapies, clinical trials and/or facilitate drug discovery.

The term "patient" is used broadly and refers to an individual that provides a biosample for testing or analysis.

Figure 8:
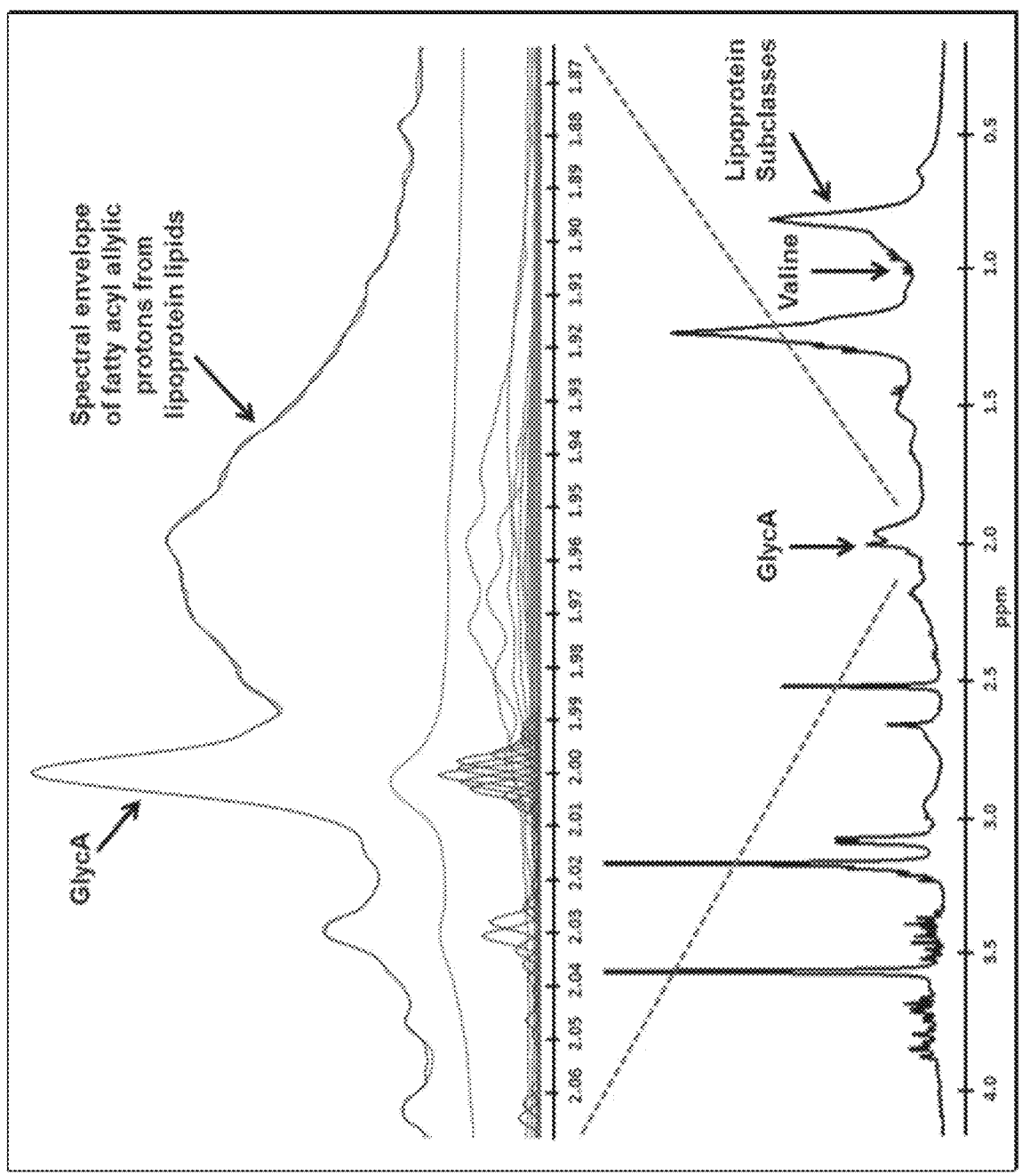
FIG. 8 is an NMR spectrum illustrating a GlycA peak region (over an enlarged view of the region) according to embodiments of the present invention.

The term "GlycA" refers to a biomarker that can be derived from a measure of composite NMR signal from carbohydrate portions of acute phase reactant glycoproteins containing N-acetylglucosamine and/or N-acetylgalactosamine moieties, more particularly from the protons of the 2-NAcGlc and 2-NAcGal methyl groups. The GlycA signal is centered at about 2.00 ppm in a plasma NMR spectrum at about 47 degrees C. (+/−0.5 degrees C.). The peak location is independent of spectrometer field but may vary depending on analysis temperature of the biosample and is not found in urine biosamples. Thus, the GlycA peak region may vary if the temperature of the test sample varies. FIG. 8 illustrates an NMR spectrum of a GlycA peak region (over an enlarged view of the region) according to embodiments of the present invention.

The GlycA NMR signal may include a subset of NMR signal at the defined peak region so as to include only clinically relevant signal contributions and may exclude a protein contribution to the signal in this region as will be discussed further below.

As used herein, the chemical shift locations (ppm) refer to NMR spectra referenced internally to CaEDTA signal at 2.519 ppm. Thus, the noted peak locations discussed and/or claimed herein may vary depending on how the chemical shift is generated or referenced as is well known to those of skill in the art. Thus, to be clear, certain of the described and/or claimed peak locations have equivalent different peak locations in other corresponding chemical shifts as is well known to those of skill in the art.

The term "biosample" refers to in vitro blood, plasma, serum, CSF, saliva, lavage, sputum, or tissue samples of humans or animals. Embodiments of the invention may be particularly suitable for evaluating human blood plasma or serum biosamples, particularly for GlycA (which is not found in urine, for example). The blood plasma or serum samples may be fasting or non-fasting. Where glucose is measured by NMR, the biosample is typically fasting blood plasma or serum samples. However, glucose may be measured by any suitable means.

The terms "population norm" and "standard" refer to values defined by a large study or studies such as the Framingham Offspring Study or the Multi-Ethnic Study of Atherosclerosis (MESA) or other study having a large enough sample to be representative of the general population. However, the instant invention is not limited to the population values in MESA or Framingham as the presently defined normal and at-risk population values or levels may change over time. Thus, a reference range associated with values from a defined population in risk segments (e.g., quartiles or quintiles) can be provided and used to assess elevated or reduced levels and/or risk of having a clinical disease state.

As used herein, the term "NMR spectral analysis" means using proton ($^1$H) nuclear magnetic resonance spectroscopy techniques to obtain data that can measure the respective parameters present in the biosample, e.g., blood plasma or blood serum.

"Measuring" and derivatives thereof refer to determining a level or concentration and/or for certain lipoprotein subclasses which can include measuring the average particle size thereof.

The term "NMR derived" means that the associated measurement is calculated using NMR signal/spectra from one or more scans of an in vitro biosample in an NMR spectrometer.

The term "lipoprotein component" refers to a lipoprotein component in a mathematical risk model associated with lipoprotein particles including size and/or concentration of one or more subclasses (subtypes) of lipoproteins. Lipoprotein components can include any of the lipoprotein particle subclasses, concentrations, sizes, ratios and/or mathematical products (multiplied) of lipoprotein parameters and/or lipoprotein subclass measurements of defined lipoprotein parameters or combined with other parameters such as GlycA.

The term "interaction parameter" refers to at least two different defined patient parameters combined (multiplied) as a mathematical product and/or ratio, typically one of the parameters is a sub-population of HDL-P and the other is an inflammatory marker. Examples of interaction parameters include, but are not limited to a sub-population of HDL, e.g., medium HDL-P ("HMP")/total HDL-P, (HMP)(GlycA), (HMP)(HZ), and/or a ratio of an inflammatory marker to a defined lipoprotein subpopulation, e.g., GlycA to HMP. The term "HZ" refers to average HDL-size. GlycA is an inflammatory biomarker. Other inflammatory biomarkers may be used in the interaction parameter, e.g., CRP (C-reactive protein), hs-CRP (high-sensitivity CRP), IL-6 (interleukin-6), fibrinogen, haptoglobin, and alpha-1-acid glycoprotein.

The terms "mathematical model" and "model" are used interchangeably and when used with STR and/or DRI ("diabetes risk index") refers to a statistical model of risk used to evaluate a subject's risk of developing type 2 diabetes in a future time period or when used with IR, refers to a risk from a model of insulin resistance (a good predictor of diabetes risk) based on one or more study populations. The STR is for a time period that is shorter than that of a longer term risk (LTR). The risk models can be or include any suitable model including, but not limited to, one or more of a logistic model, a mixed model or a hierarchical linear model. The STR and DRI risk models can provide a measure of risk based on the probability of conversion to type 2 diabetes within a defined time frame, typically within 0-3 years for STR and greater than 3 years for LTR. The STR/SDRF risk model can be for a timeframe that is less than 3 years, such as within 6 months, 1 year, 1.5 years, 2 years, 2.5 years or 3 years, post test. The IR risk can be an important risk parameter for both STR and LTR longer term risk, e.g., greater than 3 years, such as 3.5 years, 4 years, 5 years or between 5-10 years, post test.

The DRI time period can be between about 5-7 years, more typically about 5 years. The STR, IR and/or DRI risk models can stratify a risk of developing T2DM as measured by standard $\chi^2$ and/or p values (the latter with a sufficiently representative study population).

TABLE 3

MESA Follow-up Periods

| MESA Visit | Time from Baseline Exam (years) | | |
|---|---|---|---|
| Number | Mean | Minimum | Maximum |
| 2 | 1.6 | 0.9 | 3.4 |
| 3 | 3.2 | 2.1 | 4.9 |
| 4 | 4.8 | 3.3 | 6.7 |
| 5 | 9.5 | 8.1 | 11.2 |

Table 3 shows the follow-up times for the different MESA visits (follow-up exams). The STR parameter can be derived from a regression model to predict diabetes diagnosed at visit 2. Mean follow-up time was 1.6 years (0.9 yr min; 3.4 yr max). FIG. 13 shows DM diagnosed at visits 2 or 3 in MESA. The IR parameter can have any timeframe from STR to LTR, while the SDRF is only relevant in the STR. In some embodiments, the IR model can be derived from a linear regression model predicting HOMA-IR (as shown in FIG. 12).

It will be understood by those of skill in the art, almost all population studies conduct follow-up for some fixed period of time (e.g., 5 years) and do not monitor when during that time period diabetes was diagnosed. So the regression models are a cumulative measure, composed of some people who converted to diabetes sooner and others who converted later.

The term "LP-IR" score refers to a lipoprotein based insulin resistance score that rates a subject's insulin sensitivity from insulin sensitive to insulin resistant using a summation of risk scores associated with different defined lipoprotein components. See, e.g., U.S. Pat. No. 8,386,187 and Shalaurova I et al., *Lipoprotein Insulin Resistance Index: A Lipoprotein Particle—Derived Measure of Insulin Resistance*, Metabolic Syndrome and Related Disorders, Vol. 12, No. 8, October 2014, pp. 422-429, for a detailed discussion of the LP-IR score, the contents of which are hereby incorporated by reference as if recited in full herein. Generally stated, large VLDL, VLDL size, and small LDL have a positive risk association while large HDL, LDL size and HDL size have a negative association. These six components can be used to generate the LP-IR score (see, e.g., the bottom row of components indicated as associated with LP-IR in FIG. 2B), which is typically a score between 1-100, with the risk scores of individual components varying as described in Table 3 of U.S. Pat. No. 8,386,187. The LP-IR score can be calculated using NMR derived measurements of lipoproteins or other measurement methodologies.

Embodiments of the invention can employ risk models that include biomarkers that link to diabetic pathophysiology, including two or more of: insulin resistance, impaired β-cell function or impaired insulin secretion, inflammation and defective non-insulin (NI) dependent glucose uptake.

The role of HDL is complex and HDL-C is considered to be a relatively crude biomarker. Recently, researchers have suggested that HDL is an active player in diabetic pathophysiology rather than a bystander. See, Drew et al., *The Emerging Roles of HDL in Glucose Metabolism*, Nat. Rev., Endocrinol., 8, 237-245 (2012) published online 24 Jan. 2012.

The glycemic trajectory from normal to diabetic can typically be characterized by a long period of fairly stable glucose levels during which increasing insulin resistance is compensated for by increased β-cell insulin secretion, followed by an abrupt increase, generally less than about 3 years before diabetes diagnosis brought on by loss of β-cell mass and function. See, e.g., Tabak A G et al., Lancet 2009: 373: 2215-21, the contents of which are hereby incorporated by reference as if recited in full herein. Short term converters to diabetes are likely to have insulin resistance and beta-cell dysfunction or impairment. Markers associated with IR predict incident diabetes irrespective of the time frame of conversion. However, markers that, independent of IR and glucose, enhance prediction of short term conversion do not independently enhance prediction of longer term conversions provided by the IR markers.

Figure 2A:
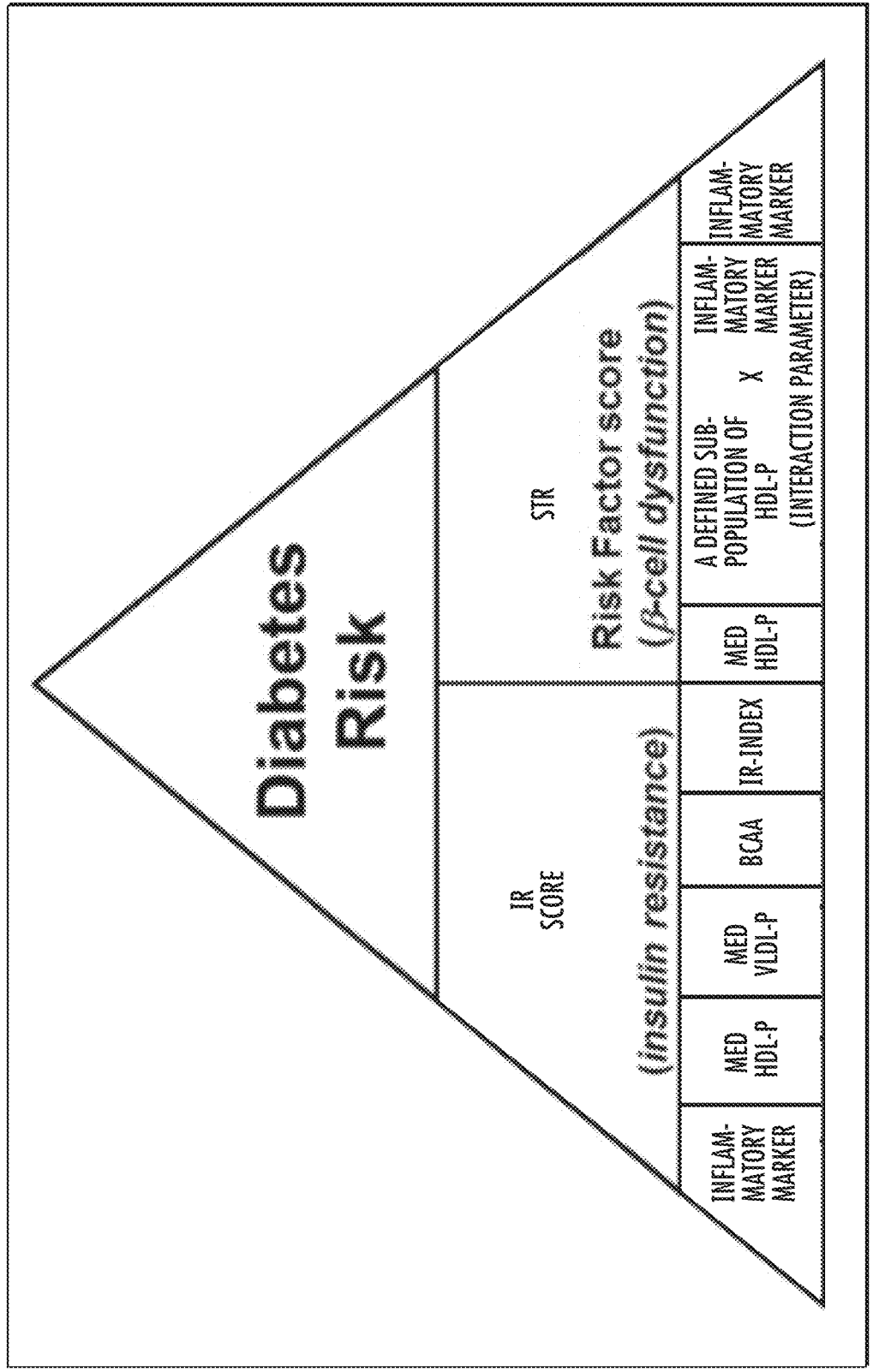
FIG. 2A is a chart illustrating diabetes risk prediction based on two separate multi-parameter risk models, one for short term risk associated with beta cell dysfunction and one for IR according to embodiments of the present invention.

Referring to FIG. 2A, embodiments of the invention provide diabetes risk evaluations using at least two separate multi-markers of lipoprotein and metabolic parameters. The two multi-marker parameters include defined lipoprotein and metabolic parameters. The two multi-marker parameters are shown as (i) an IR risk factor score for insulin resistance that includes a plurality of defined lipoprotein and metabolic parameters and (ii) a STR or SDRF risk factor score for β-cell dysfunction that includes a plurality of defined lipoprotein and metabolic parameters, some of which can overlap with the parameters used for the STR risk factor score. The STR risk factor score can include a combination of (e.g., sum of) a plurality of separate values associated with a plurality or all of the following components: medium HDL-P, an inflammatory marker and an interaction parameter. The interaction parameter can be the inflammatory marker and a defined sub-population of HDL-P, typically med HDL-P.

The IR risk factor can include only the IR index or can include the IR index and other defined lipoprotein and metabolic parameters. For example, the IR risk factor score can be generated using a combination of separate values or scores of a plurality of or all of the following components: (a) an inflammatory marker, (b) med HDL-P, (c) med-VLDL-P, (d) one or more branched chain amino acids (BCAA) and (e) an insulin resistance index with a defined numerical range. The BCAA can include one or more of Valine, Leucine and Isoleucine, which may be measured by NMR or other methodologies. See, e.g., PCT/US2013/064142, for a discussion of NMR measurement of BCAAs, the contents of which are hereby incorporated by reference as if recited in full herein.

The IR risk factor can be the LP-IR or the eLP-IR (discussed further below) or other suitable insulin resistance index. For example, an insulin resistance index using metabolites identified in US 2009/0155826 to Hu et al. ("Hu"), the contents of which are hereby incorporated by reference as if recited in full herein. Hu proposes the use of biomarkers to evaluate insulin resistance using biomarkers in one or more of Tables 4, 5, 6, 7, 8, 9A, 9B, 27, 28 and 29 (para. 98). After the level of one or more biomarker is determined, the level may be compared to disease or condition reference levels to determine a rating for each of the one or more biomarkers. The ratings can be aggregated using any algorithm to create a score, "for example, an insulin resistance (IR) score, for the subject (para. 106). Paragraph 107 goes on to give an example of an IR score of 100 indicates Type-2 diabetes, while a score of less than 25 may indicate normal glucose tolerance.

Figure 2B:
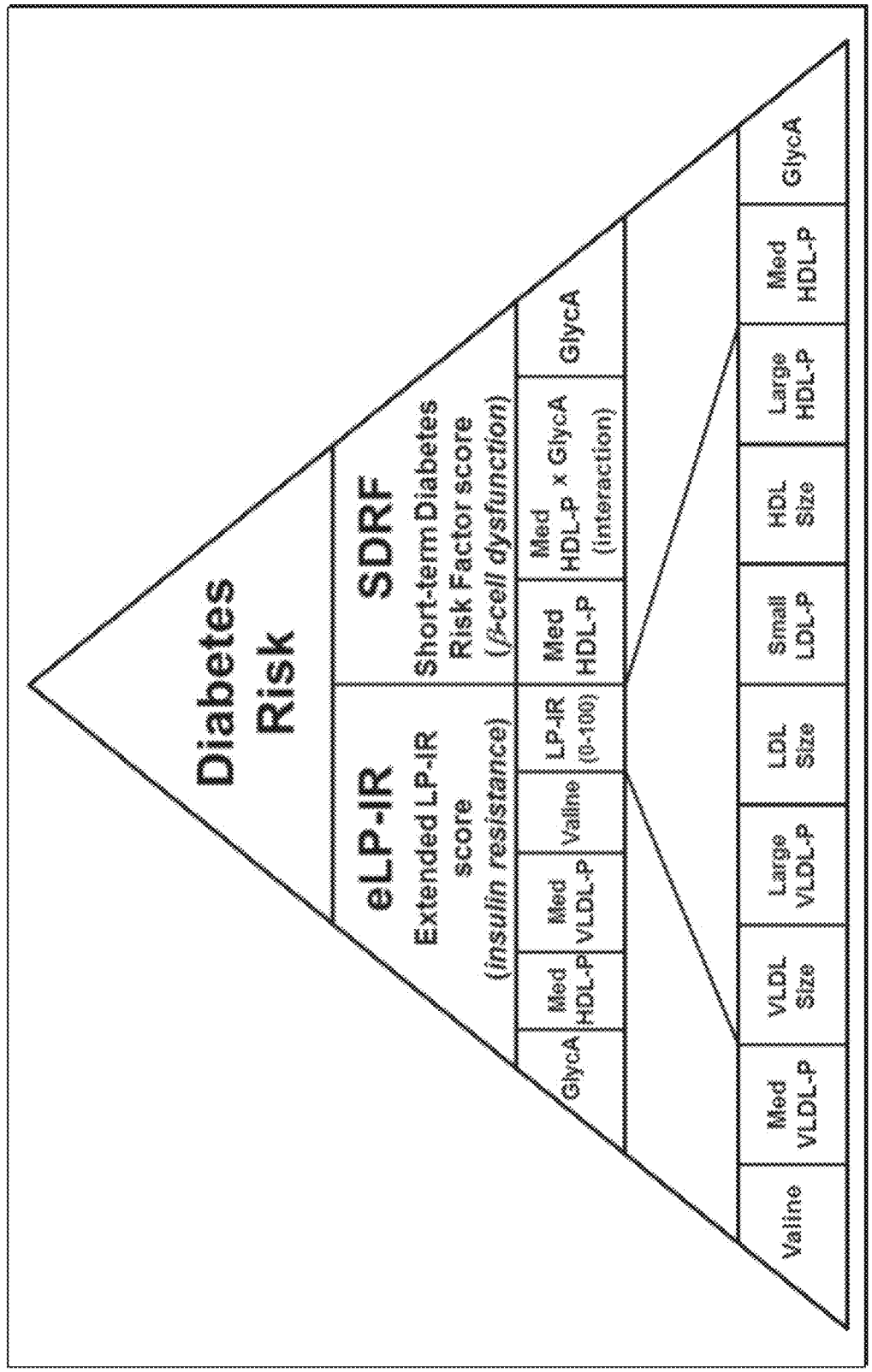
FIG. 2B is a chart illustrating diabetes risk prediction based on two separate multi-parameter risk models with exemplary particular components for the inflammatory marker and BCAA (branched chain amino acid), one for short term risk and one for insulin resistance according to embodiments of the present invention.

Referring to FIG. 2B, the two separate multimarkers of lipoprotein and metabolite parameters are shown as (i) an extended LP-IR insulin resistance ("eLP-IR") score for the IR risk factor score and (ii) short-term diabetes risk factors ("SDRF") score for the STR factor score. The SDRF score can include at least one interaction parameter, shown as GlycA×med HDL-P. The two separate risk factor scores of the multi-marker parameters can assess diabetes risk at any level of glycemia of in vitro biosamples. The biosamples can be fasting plasma biosamples.

While the eLP-IR index is shown using LP-IR by way of example, other insulin resistance indexes or scores with a defined range may be used.

The eLP-IR score is an extended version of the LP-IR score as it includes the LP-IR score (with the six noted lipoprotein components indicated by the components on the bottom of the chart within the lines extending from the LP-IR box) as well as additional defined components including, as shown, GlycA, med HDL-P, med VLDL-P, and Valine. Other BCAAs may be included or used instead of Valine, including, for example, Leucine and Isoleucine. GlycA is an inflammatory biomarker and other inflammatory biomarkers may be included or substituted for GlycA, such as, for example, fibrinogen, hs-CRP, CRP, IL-6 or haptoglobin.

Figure 9:
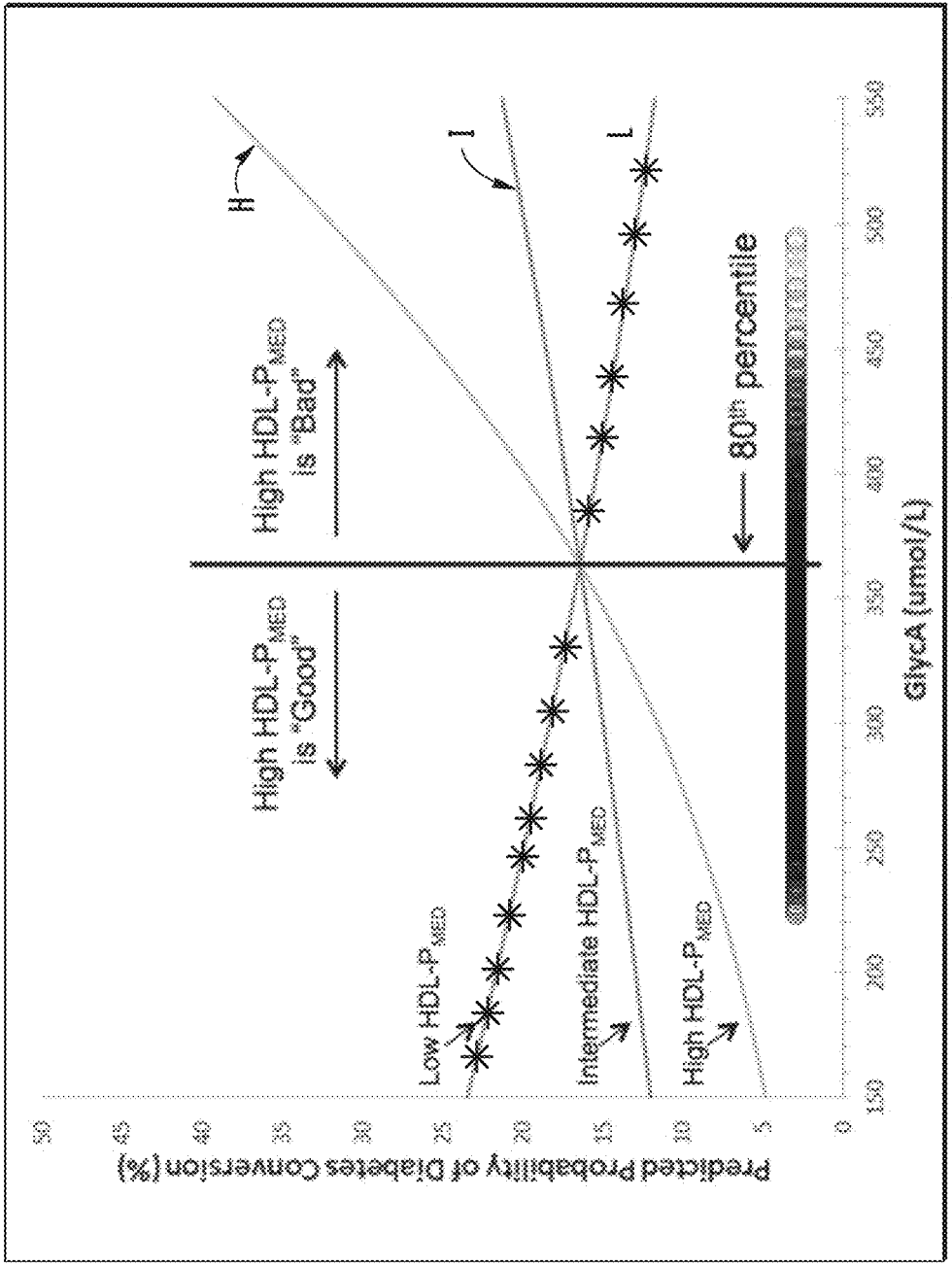
FIG. 9 is a graph of predicted short term diabetes conversion rate by GlycA level for three defined levels (high, intermediate and low) of medium HDL-P (HDL-$P_{MED}$) illustrating high levels of medium HDL-P turning from "good" to "bad" at about an $80^{th}$ percentile level of GlycA (relative to a population norm) according to embodiments of the present invention.

The SDRF score can include med HDL-P and at least one inflammatory marker, shown as GlycA, as well as at least one interaction parameter. The interaction parameter is not used in the eLP-IR or LP-IR scores as it is not associated with longer term risk (it is not statistically associated with insulin resistance but is associated with diabetes risk). Again, a different inflammatory marker or interaction parameter may be used. Notably, the interaction parameter, e.g., the interaction of HDL-$P_{MED}$ and GlycA is believed to reflect a relationship of these variables with β-cell dysfunction. The results provide epidemiologic support for recent evidence for multiple roles of HDL in diabetic pathophysiology and for the modulation of HDL functionality by inflammation. FIG. 9 graphically illustrates the modulation of HDL functionality, e.g., changing from negative to a positive risk factor as the level of the inflammation, as assessed by GlycA, increases. While shown as at about the $80^{th}$ percentile of GlycA for MESA, a $65^{th}$ percentile value was identified using IRAS, both at a level of about 350 to 360 µmol/L.

The mathematical models can use other clinical parameters such as gender, age, BMI, whether on hypertension medicine, glucose and the like.

While it is contemplated that the STR, IR and DRI parameters can be provided as numerical scores within a defined numerical range, with lower scores associated with lower risk and higher scores associated with higher risk of conversion to diabetes, the risk scores or indexes can be presented on a patient report in different manners. The STR, IR and DRI scores can be provided as a result expressed numerically or alphanumerically, typically comprising a numerical score on a defined scale or within a defined range of values. For example, in particular embodiments, the STR, IR and/or DRI scores can be provided as or include a score within a defined range, such as, for example, between 0 and 1, on the low end, to 10 or 100 on the high end. Examples of ranges include: 0-0.1, 0-1, 0-5, 0-10, 1-10, 0-24, 1-24, 0-100, 1-100, 10-100, 0-1000, 1-1000, 10-1000 and the like. Typically, the lowest number is associated with the least risk and the higher numbers are associated with increased risk of developing T2DM in the future. The lower value in the range may be above "0" such as 1, 2, 3, 4 or 5 and the like, or may even be a negative number (e.g., −1, −2, −3, 4, −5 and the like). Other index examples, include, for example, alphanumeric indexes or even icons noting degrees of risk, including but not limited to, "LR1" (low risk), IR5 (intermediate risk) and "HR9" (high risk), terms such as "DRI positive", "DRI high", "DRI neutral", "DRI low", "DRI good", "DRI bad", "DRI watch" and the like.

The IR, STR or DRI scores can all be between 0-10 or 1-10.

Figure 10:
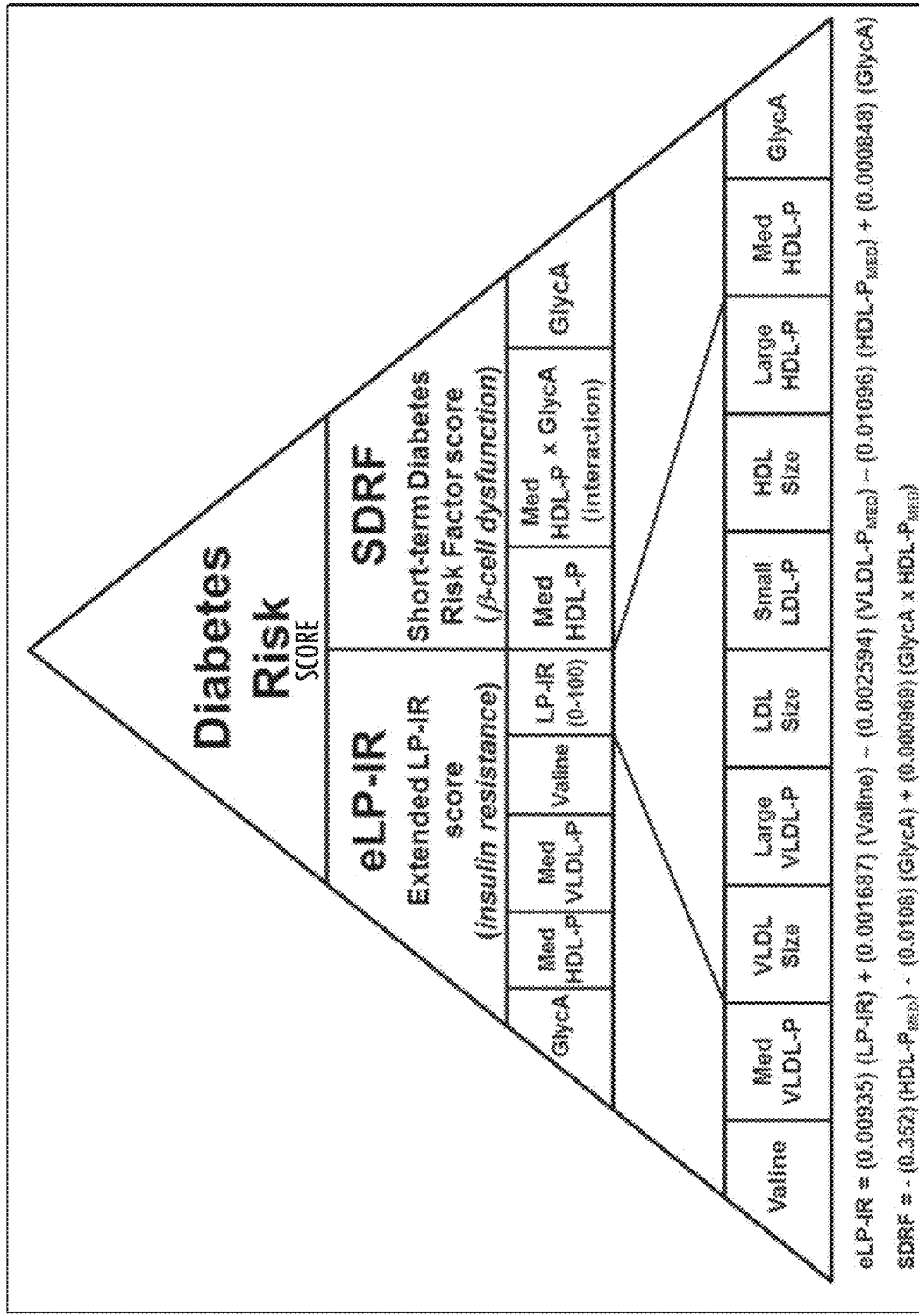
FIG. 10 is a block diagram similar to FIG. 2, illustrating exemplary coefficients that may be used with the noted respective components to generate eLP-IR and SDRF scores, which may be used alone or combined to form a DRI score according to embodiments of the present invention.

The IR score and the SDRF scores can have a range that is between 0-100 or 1-100 and DRI score can have a range of 0-10 or 1-10 as the risk models can apply a defined small coefficient to the different components of the respective risk models, e.g., a value that is less than 0.001 to the IR score, typically about 0.009 (FIG. 10).

As noted above, the STR, IR and DRI diabetes risk indexes or scores can be decoupled from glucose measurements. Thus, for example, one or more of the STR, IR or DRI scores can be calculated for patients as a screening test or to stratify risk independent of glucose. That is, the STR/IR or DRI can be used to stratify risk for patients with glucose levels below 110 mg/dL, e.g., between 80-110 mg/dL and/or can predict diabetes conversion independent of fasting glucose or other measure of glycemia.

To help understand the information provided by the two different measurements of SDRF and IR, instructional guidelines and/or an electronic program can be provided to a clinician that generates a test result when both data points are supplied. The combined data evaluation can be provided as a download from a laboratory or from an offering company, such as, for example, LipoScience (Raleigh, N.C.). Instructional guidelines can be provided to a clinician so that the clinician can understand the risk stratification provided by the STR and/or DRI scores and can inform a clinician whether to order a glucose challenge test which may be more time consuming, expensive or inconvenient for a patient. An electronic risk analysis circuit can also be provided (e.g., a portal accessible via the Internet) that can generate risk information based on STR, IR and/or DRI scores.

The STR/SDRF, IR and/or DRI scores can be generated independent of and/or without requiring concurrent glucose measurements and may be used to allow a clinician to consider what risk category a respective patient may belong to.

Lipoproteins include a wide variety of particles found in plasma, serum, whole blood, and lymph, comprising various types and quantities of triglycerides, cholesterol, phospholipids, sphyngolipids, and proteins. These various particles permit the solublization of otherwise hydrophobic lipid molecules in blood and serve a variety of functions related to lipolysis, lipogenesis, and lipid transport between the gut, liver, muscle tissue and adipose tissue. In blood and/or plasma, lipoproteins have been classified in many ways, generally based on physical properties such as density or electrophoretic mobility or measures of apolipoprotein A-1 (Apo A-1), the main protein in HDL.

Classification based on nuclear magnetic resonance-determined particle size distinguishes distinct lipoprotein particles based on size or size ranges. For example, the NMR measurements can identify at least 15 distinct lipoprotein particle subtypes, including at least 5 subtypes of high density lipoproteins (HDL), at least 4 subtypes of low density lipoproteins (LDL), and at least 6 subtypes of very low density lipoproteins (VLDL), which can be designated TRL (triglyceride rich lipoprotein) V1 through V6.

The NMR derived estimated lipoprotein sizes, e.g., HDL-P particle sizes for H1-H26, are not exact but are approximate to estimate each subclass to a size range. Other methodologies may provide different size ranges that correlate to the NMR estimated subclass sizes.

Further, it is also noted that while NMR measurements of the lipoprotein particles are particularly suitable for the analyses described herein, it is contemplated that other technologies may be used to measure these parameters now or in the future and embodiments of the invention are not limited to this measurement methodology. It is also contemplated that different protocols using NMR may be used (e.g., including different deconvolving protocols) in lieu of the deconvolving protocol described herein. See, e.g., Kaess et al., The lipoprotein subfraction profile: heritability and identification of quantitative trait loci, J Lipid Res. Vol. 49 pp. 715-723 (2008); and Suna et al., 1H NMR metabolomics of plasma lipoprotein subclasses: elucidation of metabolic clustering by self-organizing maps, NMR Biomed. 2007; 20: 658-672. Flotation and ultracentrifugation employing a density-based separation technique for evaluating lipoprotein particles and ion mobility analysis are alternative technologies for measuring lipoprotein subclass particle concentrations. Vertical auto profile methodology or other subfractionation methods may potentially be used. See, Martin et al., High-density lipoprotein subfractions: Current views and clinical practice applications, Trends Endocrinol Metab, 2014; 25; 329-336, the contents of which are hereby incorporated by reference as if recited in full herein.

Figure 3A:
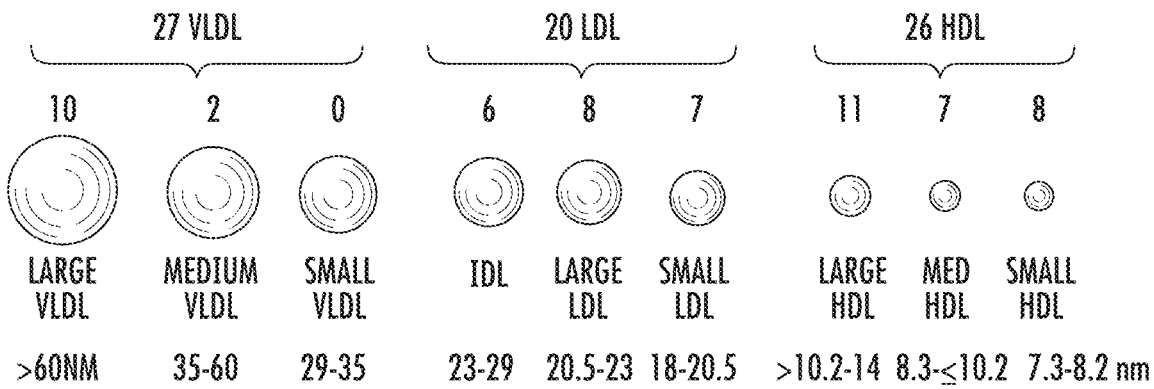
FIGS. 3A and 3B illustrate subpopulations of lipoproteins with exemplary size ranges according to embodiments of the present invention.
Figure 3B:
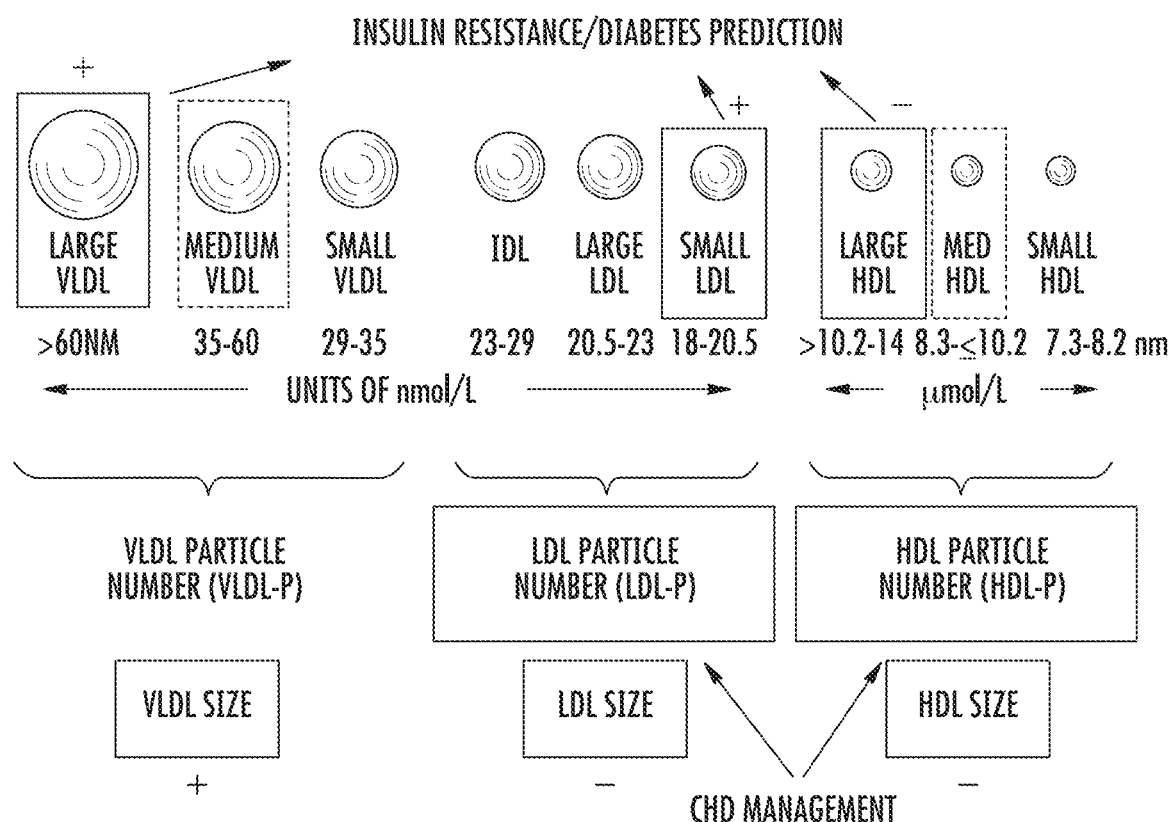

Lipoprotein subclass grouping can include subclasses with concentrations that can be summed to determine VLDL-P, HDL-P and LDL-P numbers according to some particular embodiments of the present invention. It is noted that the "small, large and medium" size ranges noted can vary or be redefined to widen or narrow the upper or lower end values thereof or even to exclude certain ranges within the noted ranges. The particle sizes noted typically refer to average measurements, but other demarcations may be used. FIGS. 3A and 3B illustrate exemplary size ranges for different sub-populations of lipoproteins. Embodiments of the invention classify lipoprotein particles into subclasses grouped by size ranges based on functional/metabolic relatedness as assessed by their correlations with lipid and metabolic variables. Thus, as noted above, the evaluations can measure over 20 discrete subpopulations (sizes) of lipoprotein particles, typically between about 30-80 different size subpopulations (or even more).

For the GlycA measurement calculations, where used, the discrete number of HDL and LDL groupings can be less than those used to quantitatively measure the lipoprotein subclasses (where NMR is used for the lipoprotein measurements). The subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med. 2006; 26: pp. 847-870, the contents of which are hereby incorporated by reference as if recited in full herein.

The term "LDL-P" refers to a low density lipoprotein particle number (LDL-P) measurement (e.g., LDL-P number) that sums the concentration of defined LDL subclasses. Total LDL-P can be generated using a total low density lipoprotein particle (LDL-P) measurement that sums the concentration (μmol/L) of all the LDL subclasses (large and small) including sizes between 18-23 nm. In some embodiments, the LDL-P measurement may employ selected combinations of the LDL subclasses (rather than the total of all LDL subclass subpopulations). As used herein, the term "small LDL particles" typically includes particles whose sizes range from between about 18 to less than 20.5 nm, typically between 19-20 nm. The term "large LDL particles" includes particles ranging in diameter from between about 20.5-23 nm. It is noted that the LDL subclasses of particles can be divided in other size ranges. For example, the "small" size may be between about 19-20.5 nm, intermediate may be between about 20.5-21.2 nm, and large may be between about 21.2-23 nm. In addition, intermediate-density lipoprotein particles ("IDL" or "IDL-P"), which range in diameter from between about 23-29 nm, can be included among the particles defined as "large" LDL (or even small VLDL). Thus, for example, the LDL subclasses can be between 19-28 nm.

The term "HDL-P" refers to a high density lipoprotein particle number (HDL-P) measurement (e.g., HDL-P number) of a concentration of a defined sub-population of lipoprotein subclasses. Total HDL-P can be generated using a total high density lipoprotein particle (HDL-P) measurement that sums the concentration (μmol/L) of all the HDL subclasses (which may be grouped based on size into different size categories such as large, medium and small) in the size range between about 7 nm to about 15 nm, typically between 7.3 or 7.4 and 13.5 or 14 nm.

HDL subclass particles typically range from between about 7 nm to about 15 nm, more typically about 7.3 nm to about 14 nm (e.g., 7. 4 nm-13.5 nm). The HDL-P concentration, at least when measured by certain methodologies including NMR deconvolution, is the sum of the particle concentrations of the respective subpopulations of its HDL-subclasses. The HDL subpopulation can include medium HDL particle subclasses (HMP). Medium HDL-P, which is referred to interchangeably herein using the abbreviations "HMP" or "HDL-$P_{MED}$" or "med-HDL-P", refers to a defined sub-population of HDL particles that excludes small and large HDL particle subclasses. The exact size range of HMP/med-HDL-P/HDL-$P_{MED}$ may vary between measurement methodologies and study populations.

However, as is well known to those of skill in the art, HMP/med-HDL-P/HDL-$P_{MED}$, as well as the other lipoprotein subpopulations used in the different IR/STR risk models can be selected to maximize correlation of risk of conversion to diabetes using a risk model (typically a logistic regression model of at least one defined study population), either, or both, in the short term or longer term multi-parameter STR and IR risk models.

Figure 5:
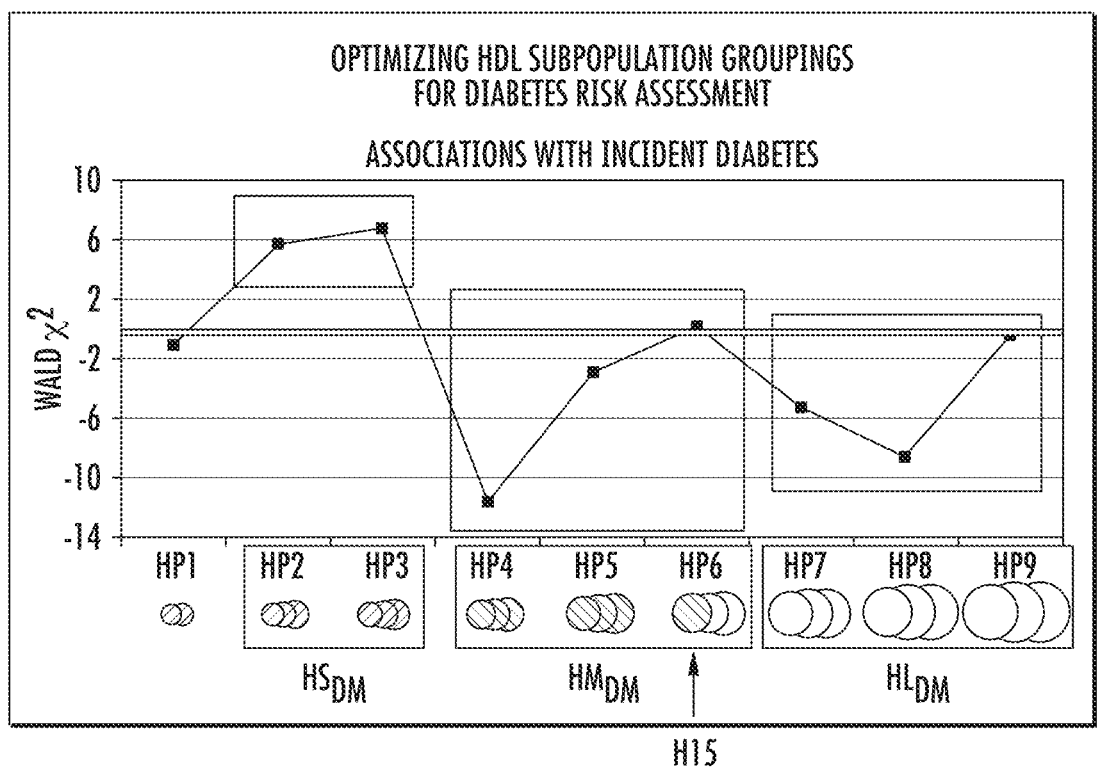
FIG. 5 is a graph showing risk associations for different sub-populations of HDL per the size groupings in FIG. 4 according to embodiments of the present invention.

FIG. 5 graphically illustrates HDL subpopulations grouped by sizes and incident diabetes risk associations from MESA. As noted herein, the HDL sizes of the HDL-PMED subclass can vary and can depend on risk associations in a study population, this graph shows negative and positive associations with different groupings of sizes by way of example only. The graph illustrates diabetes risk associations for 9 different size groupings or sub-populations of the 26 HDL subpopulations with three boxes of further groupings of selected HDL subclasses according to embodiments of the present invention. The $\chi 2$ values from the logistic regression model indicate the strengths and signs of the risk associations as determined in the MESA study population during 6 years of follow-up among 4968 MESA participants with 411 incident cases of diabetes diagnosed (all 9 subpopulations were included in the same logistic regression model, adjusted for age, gender, race, and glucose).

In some embodiments, the different subpopulations of HDL-P can be identified by a number from 1-26, with "1" representing the smallest size subpopulation in the HDL class and "26" being the largest size subpopulation in the HDL class as shown in FIG. 4.

HMP can include, for example, HDL particles with sizes corresponding to H9-H14, or H9-H15, and optionally H9-H17, of respective subpopulations. FIG. 4 illustrates the optional different exemplary subclass groupings that can be used to define the med-HDL-P subpopulation. These size categories can be selected to optimize risk stratification for individuals having an intermediate risk in a population norm based on (fasting) glucose measurements of 90 mg/dL (or even less) to 110 mg/dL. That is, the lipoprotein subclass sub-populations or groups for a particular parameter can be selected based on a statistical analysis of study populations such as MESA, IRAS and/or Framingham to determine how the various subpopulations should be grouped based on risk association with T2DM, rather than LP-IR or insulin resistance.

In some embodiments, medium HDL-P (HMP/HDL-$P_{MED}$) can be associated with HDL-P in the range of one of: 8.3-9.2 nm, 8.3-9.4 nm, 8.3-9.7 nm, 8.3 to 10 nm or 8.3 nm to 10.2 nm (estimated sizes based on NMR measurements).

Diabetes prediction performance in the IRAS study dataset was better with a somewhat narrower size range and not much worse in the MESA study dataset (which yielded a medium HDL-P span of 8.3 nm to 10.0 nm). However the upper range for medium HDL-P can be 9.4 nm, 10.0 nm or 10. 2 nm, or even slightly higher or lower, for example.

The term "large VLDL particles" refers to particles at or above 60 nm such as between 60-260 nm. The term "medium VLDL particles" ("medVLDL-P" or "VLDL-Pmed") refers to particles with sizes between 35-60 nm. The term "small VLDL particles" refers to particles between 29-35 nm. The term "VLDL-P" refers to a very low density lipoprotein particle number (VLDL-P) measurement (e.g., VLDL-P number) that sums the concentration of defined VLDL subclasses. Total VLDL-P can be generated by summing the concentrations (nmol/L) of all the VLDL subclasses (large, medium and small). The exact size range for medium and large VLDL may vary between measurement methodologies and study populations but each is associated with a defined sub-population of lipoproteins which can be defined based on risk associations of different sub-class groupings.

As noted above, embodiments of the present invention provide STR, IR and DRI scores using defined mathematical models of risk of different defined lipoprotein and metabolite biomarkers or parameters of an in vitro biosample(s) of a patient or subject to identify at-risk patients or subjects before onset of T2DM who may benefit from pharmaceutical, medical, diet, exercise or other intervention.

One or more of the STR, IR and/or DRI scores can also or alternatively be used during clinical trials and/or for drug discovery to monitor for positive or negative changes in metabolic or cellular function.

The STR, IR and/or DRI evaluation can be decoupled from a glucose measurement and can relatively easily be generated as a screening tool and may be able to identify at-risk individuals earlier in time than with conventional tests.

An "unprocessed biosample" as used herein refers to a biosample that, unlike sample preparation for mass spectrometry analysis, is not subjected to processing that causes the biosample to be physically or chemically altered after it is obtained (but buffers and diluents can be used). Thus, once the biosample is obtained, components from the biosample are not altered or removed. For example, once a blood serum biosample is obtained, the serum is not subjected to processing that removes components from the serum. In some embodiments, an unprocessed biosample is not subjected to filtering and/or ultrafiltration processes.

In some embodiments, a patient glucose measurement can be obtained via NMR analysis of the biosample NMR spectrum, along with lipoprotein particle measurements, GlycA and Valine measurements. However, glucose measurements, where used, can alternatively be obtained in conventional chemical ways.

In some particular embodiments, it is contemplated that NMR measurements of GlycA, Valine, and lipoproteins of a single (blood/plasma) in vitro biosample can be analyzed to provide important clinical information and/or further improve a prediction or evaluation of a patient or subject's risk of developing type 2 diabetes and/or having prediabetes in the future.

Figure 6A:
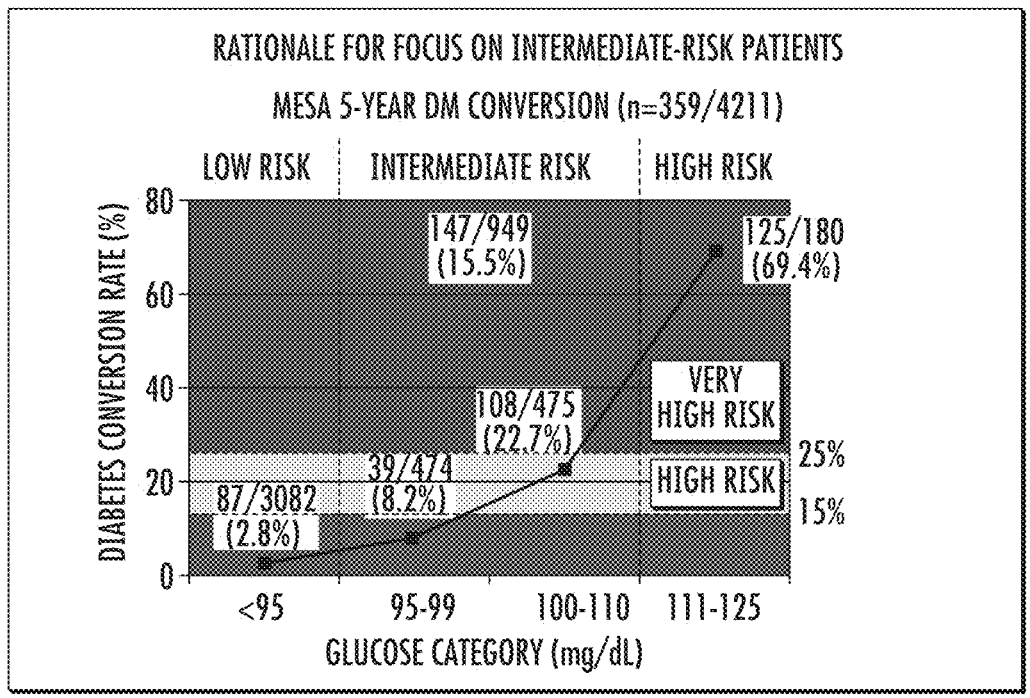
FIG. 6A is a graph of diabetes conversion rate versus glucose category (low risk, intermediate risk, high risk) based on MESA 5-year T2DM conversion (n=359/4211) illustrating an unmet need for stratifying or better identifying patients at increased risk of progression to T2DM for intermediate risk glucose patients according to embodiments of the present invention.
Figure 6B:
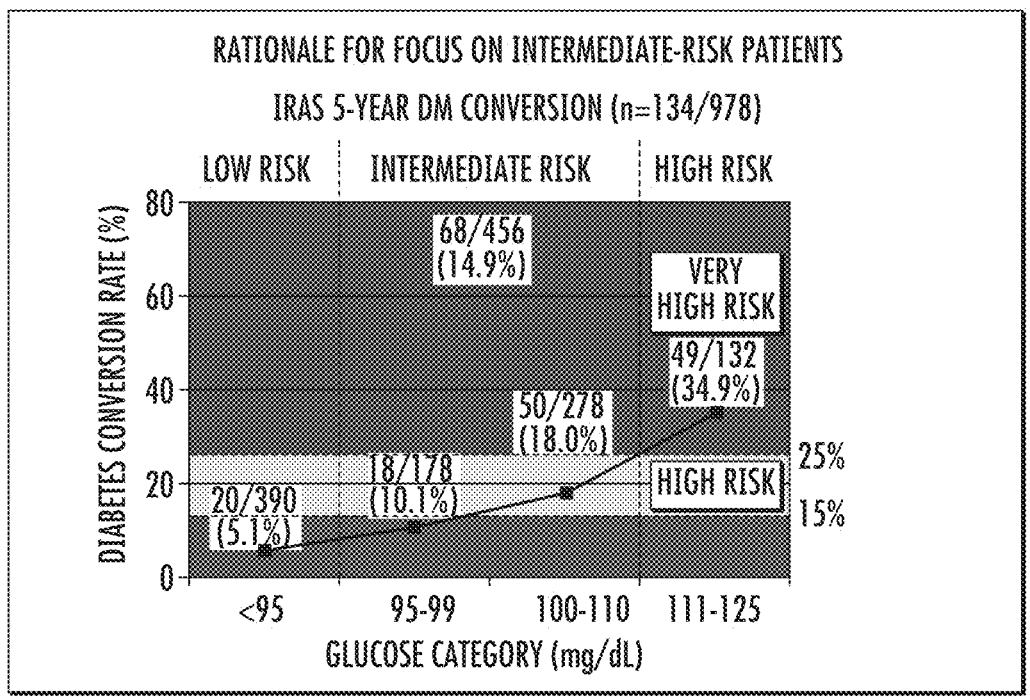
FIG. 6B is a graph of diabetes conversion rate versus glucose category (low risk, intermediate risk, high risk) based on IRAS 5-year T2DM conversion (n=134/978) illustrating an unmet need for stratifying or better identifying patients at increased risk of progression to T2DM for intermediate risk glucose patients according to embodiments of the present invention.

FIG. 6A is a graph of diabetes conversion rate versus glucose category (low risk, intermediate risk, high risk) based on MESA 5-year T2DM conversion (n=359/4211) illustrating an unmet need for stratifying or better identifying patients at increased risk of progression to T2DM for intermediate risk glucose patients according to embodiments of the present invention. FIG. 6B is a graph of diabetes conversion rate versus glucose category (low risk, intermediate risk, high risk) based on IRAS 5-year T2DM conversion (n=134/978) also illustrating an unmet need for stratifying or better identifying patients at increased risk of progression to T2DM for, particularly for those deemed to be in the low or intermediate risk glucose region according to embodiments of the present invention. FIGS. 6A/6B contrast the risk assigned on the basis of glucose level ("low"<100; "high">=100 as implied by the designation of "prediabetes" for glucose levels in the elevated rage of 100-125) and actual risk shown on they axis categorized (implicitly) as not high (<15% 5-year conversion), "high" 15-25%, and "very high" (>25%). In MESA, for example, 39+87 "low risk" people with glucose <100 developed diabetes, so their risk was not actually low. The DRI scores provided by embodiments of the invention can subdivide putatively "low risk" individuals into those with truly low risk and others with high or even very high risk (shown better by the wide ranges of predicted diabetes rates within each glucose category).

FIG. 7 is a chart of the characteristics of the MESA study population (n=3450).

FIG. 8 is a graph of NMR spectra showing the GlycA, Valine and lipoprotein subclasses peak regions.

FIG. 9 is a graph of predicted short term diabetes conversion rate by GlycA level (μmol/L) for three defined levels of HDL-$P_{MED}$ (high, intermediate and low) illustrating high HDL-$P_{MED}$ turns from "good" to "bad" at about an $80^{th}$ percentile level of GlycA. The high HDL-PMED line is represented by the low line on the left side which rises to the higher risk top line on the right. The low HDL-$P_{MED}$ line is shown with the stars on the line illustrating its decreasing risk association as GLycA levels rise (when inflammation increases).

The HDL-$P_{MED}$ values can be 9, 12.9 and 17.17, representing $25^{th}$, $50^{th}$ and $75^{th}$ percentiles. The predicted probabilities for conversion to diabetes for short term conversion to diabetes in MESA (n=181/3450) can be based on the logistic regression for a prophetic 60 year old Caucasian female with fasting plasma glucose (FPG)=105 mg/dL and $50^{th}$ percentile eLP-IR score (0.90).

The concentration range of GlycA is typically between about 220 to 500 μmol/L, inclusive thereof.

FIG. 10 is a block diagram similar to FIG. 2B, illustrating exemplary mathematical equations with exemplary coefficients that may be used with the noted respective components to generate eLP-IR and SDRF scores. The eLP-IR score can be combined with the SDRF score to generate a DRI score. In some embodiments, each score can be provided or one of the different scores can be provided to a user for evaluation.

The eLP-IR score typically ranges from about 0.1 to 1.8 and can be reported to a patient and/or clinician in percentile values using a population norm such as MESA as a reference population.

The SDRF score typically ranges between from about −6.4 to −1.6 and can also be reported in percentile units.

The DRI score is typically transformed for reporting purposes to have a range between 1 and 10. That is, the exemplary the ranges given here are for the "raw" output values of eLP-IR and SDRF, i.e., the values produced by the 2 equations at the bottom of the FIG. 10 pyramid. For reporting purposes, the SDRF and eLP-IR values can be mathematically altered/transformed into percentile values (giving 1-100 scores, for example).

Figure 11A:
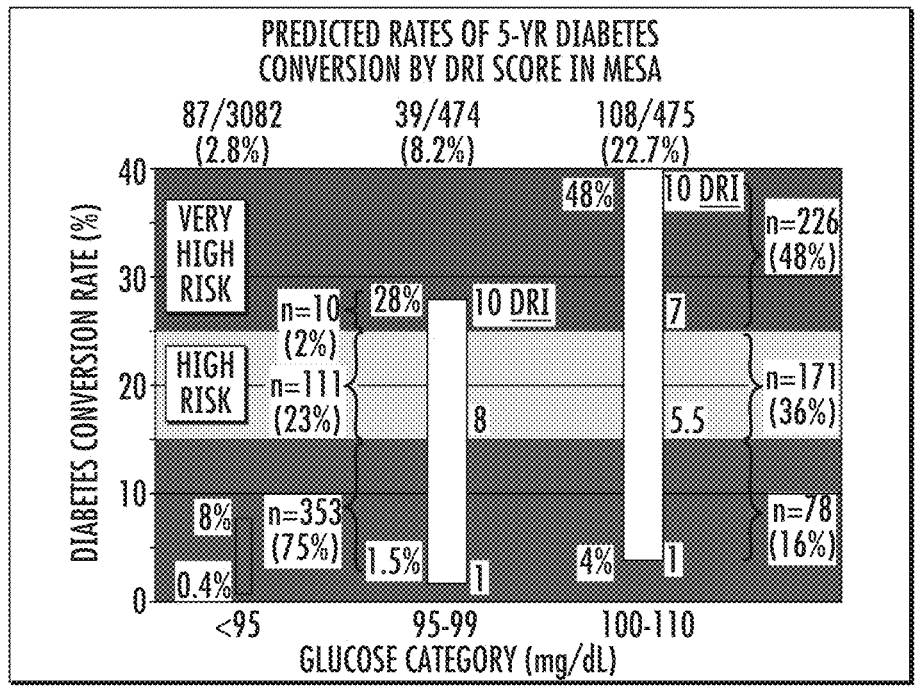
FIG. 11A is a graph of predicted diabetes conversion rates (%) versus glucose category in mg/dL units by DRI score (n=1-10) in Multi-Ethnic Study of Atherosclerosis (MESA) according to embodiments of the present invention.

FIG. 11A is a graph showing vertical rectangles of with ranges of DRI-predicted diabetes conversion rates (%) for participants in the MESA study within the glucose categories of <95 mg/dL, 95-99 mg/dL and 100-110 mg/dL, respectively, to illustrate how the DRI score can stratify the risk of persons within the same narrow glucose range.

Figure 11B:
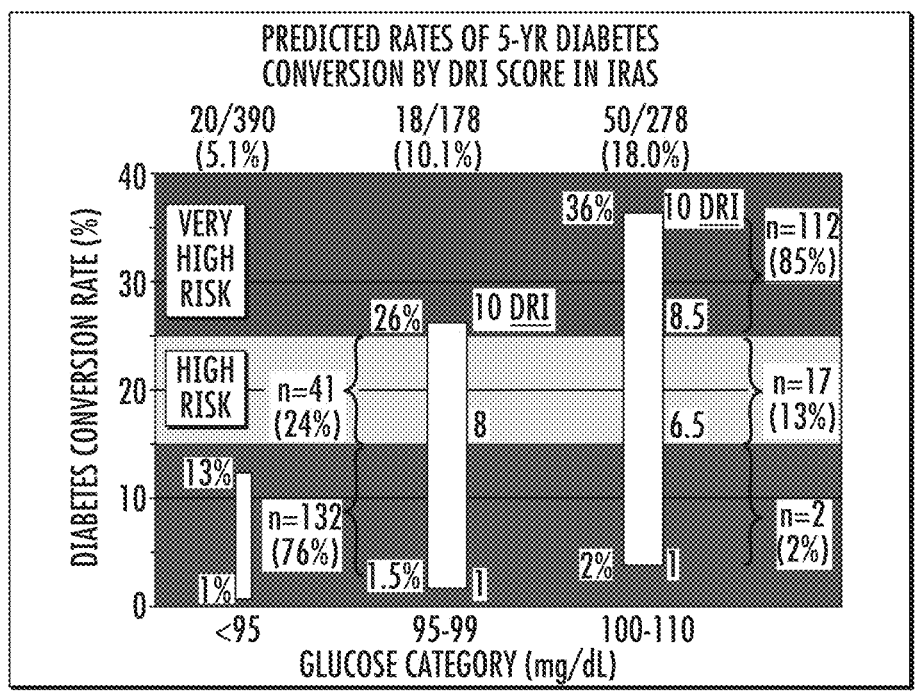
FIG. 11B is a graph of predicted diabetes conversion rates (%) versus glucose category in mg/dL units by DRI score (n=1-10) in IRAS (Insulin Resistance Atherosclerosis Study) according to embodiments of the present invention.

FIG. 11B is a similar graph showing the ranges of DRI-predicted diabetes conversion rates (%) for participants in the IRAS study within the glucose categories of <95 mg/dL, 95-99 mg/dL and 100-110 mg/dL according to embodiments of the present invention, which validates that MESA derived DRI risk models can stratify a person's risk within the same glucose range.

FIG. 12 is a chart showing the parameters included in three linear regression models predicting insulin resistance (as assessed by HOMA-IR) in MESA (n=3446). Strengths of association of each parameter with insulin resistance are given as the difference in ln (HOMA-IR) per one standard deviation increment. eLP-IR can be represented by Model 2 parameters with the noted exemplary beta-coefficients in Equation 2A contributing to the eLP-IR multimarker parameter of insulin resistance according to embodiments of the present invention. Equation 2B is a more generalized version of Equation 2A recognizing the coefficient values (shown by A-E) can vary from those shown in Equation 2A (based on a different study population and/or on a different inflammatory marker, different IR or a different BCAA parameter, for example).

$$\text{eLP-IR} = (0.00935)(\text{LP-IR}) + (0.001687)(\text{Valine}) - (0.002594)(\text{VLDL-}P_{MED}) - (0.01096)(\text{HDL-}P_{MED}) + (0.000848)(\text{GlycA}) \quad \text{Equation 2A}$$

$$\text{eLP-IR} = (A)(\text{LP-IR}) + (B)(\text{Valine}) - (C)(\text{VLDL-}P_{MED}) - (D)(\text{HDL-}P_{MED}) + (E)(\text{GlycA}) \quad \text{EQUATION 2B}$$

FIG. 13 is a chart of parameters contributing to the SDRF multimarker parameter of short term risk according to embodiments of the present invention, from logistic regression in MESA with short-term (n=181/3450) or long-term (n=286/3269) diabetes conversion as dependent variable. Strengths of association of each parameter in the different models are given by the odds ratio (OR) per one standard deviation increment. SDRF was derived using Equation 3A using beta-coefficients from Model 4 for short-term diabetes conversion. Equation 3B is a more generalized version of Equation 3A recognizing the coefficient values (shown by A-C) can vary from those shown in Equation 3A (based on different study populations and/or on a different inflammatory marker, or a different interaction parameter, for example).

$$\text{SDRF} = -(0.352)(\text{HDL-}P_{MED}) - (0.0108)(\text{GlycA}) + (0.000969)(\text{GlycA} \times \text{HDL-}P_{MED}) \quad \text{EQUATION 3A}$$

$$\text{SDRF} = -(A)(\text{HDL-}P_{MED}) - (B)(\text{GlycA}) + (C)(\text{GlycA} \times \text{HDL-}P_{MED}) \quad \text{EQUATION 3B}$$

The "raw" eLP-IR and SDRF risk scores from EQUATIONS 2A and 3A, respectively, can be transformed for reporting purposes into respective scores in a range between 1-100 based on percentile values within a reference population such as MESA. In such case of eLP-IR, values <0.7 (<$25^{th}$ percentile) and >1.1 (≥$75^{th}$ percentile) could signify a low and high risk, respectively, for developing type 2 diabetes. In the case of SDRF, values <−4.1 (<$25^{th}$ percentile) and ≥−3.8 (≥$75^{th}$ percentile) could indicate a low and high risk, respectively, of converting to diabetes within a relatively short time period. Examples of ranges of raw scores for SDRF and eLP-IR are provided in Table 4 below.

TABLE 4

Percentile Values in MESA for eLP-IR and SDRF scores

| | Minimum | Maximum | $25^{th}$ percentile | $50^{th}$ percentile | $75^{th}$ percentile |
|---|---|---|---|---|---|
| eLP-IR | 0.1 | 1.7 | 0.7 | 0.9 | 1.1 |
| SDRF | −6.4 | −1.6 | −4.1 | −3.9 | −3.8 |

The defined HDL-P subpopulation for IR (e.g., eLP-IR) may differ from the HDL-P subpopulation used for SDRF but is typically the same concentration measurement of the same defined HDL-P subpopulation used to calculate the SDRF score.

SDRF and eLP-IR scores or parameters can be combined into a composite or cumulative DRI score. In some embodiments, the SDRF and IR score (e.g., eLP-IR) coefficients (weights) can be selected/defined using a logistic regression model for 5-year diabetes conversion in people with glucose <110 mg/dL. MESA or other data can be used for that purpose. The selected weighting factors can be validated in a different study in assessing 5-year risk in IRAS.

Logistic models in both MESA (5-y) and IRAS (5-y) as well as MESA longer-term (~10-y) were generated to provide examples of coefficients and chi-square values for SDRF and eLP-IR in those 3 situations. These are only examples as the eLP-IR and/or SDRF components, e.g., Valine or GlycA assays may be adjusted or other IR models/scores, other inflammatory markers or other BCAAs may be used, for example. As is well known to those of skill in the art, the logistic models can be run with the different components to select/define the coefficients. Table 5 is a chart showing exemplary coefficients that can be used to provide the X and Y factors (Equation 1) for the DRI scores, with SDRF having almost no value in the 10 year conversion.

TABLE 5

Exemplary X and Y coefficients for DRI scores.

| Model | Parameter | Coefficient | Model $\chi^2$ | AUC | Parameter $\chi^2$ | p |
|---|---|---|---|---|---|---|
| MESA 5-year conversion among participants with glucose <110 mg/dL (n = 270/4751) | | | | | | |
| age, sex, race, glucose | — | — | 296.2 | 0.774 | — | — |
| +eLP-IR + SDRF | e-LP-IR | 2.1017 | 360.2 | 0.805 | 46.6 | <0.0001 |
| | SDRF | 0.5163 | | | 6.55 | 0.01 |
| MESA 10-year conversion among participants | | | | | | |

TABLE 5-continued

Exemplary X and Y coefficients for DRI scores.

| Model | Parameter | Coefficient | Model $\chi^2$ | AUC | Parameter $\chi^2$ | p |
|---|---|---|---|---|---|---|
| with glucose <110 mg/dL (n = 362/3319) | | | | | | |
| age, sex, race, glucose | — | — | 328.0 | 0.766 | — | — |
| +eLP-IR + SDRF | e-LP-IR SDRF | 2.4475 0.0391 | 411.8 | 0.801 | 74.0 0.04 | <0.0001 ns |
| IRAS 5-year conversion among participants with glucose <110 mg/dL (n = 88/844) | | | | | | |
| age, sex, race, glucose | — | — | 48.55 | 0.715 | — | — |
| +eLP-IR + SDRF | e-LP-IR SDRF | 2.2294 0.7292 | 79.7 | 0.776 | 14.7 13.0 | 0.0001 0.0003 |

In some embodiments, the "raw" DRI values can range from about −3.0 to about +1.8, but other raw score ranges are possible. The DRI raw scores may optionally be transformed into a defined standardized score range of 1-10 or 0-10, for example.

Thus, for example, in some embodiments, using the first set of coefficients (MESA 5-year) the DRI equation can be: DRI=2.1017 (eLP-IR)+0.5163 (SDRF).

In some embodiments, rather than using percentiles, the DRI range can be segmented into up into a set of equal parts, e.g., 10-50, typically 20, equal parts to transform the raw values into DRI score values ranging from 1-10 in 0.5 increments (i.e., 0.5, 1.0, 1.5, . . . 10) to provide the risk assessment, each with larger values representing increased risk over lower values.

FIG. 14 is a chart illustrating the conversion to diabetes during a 5.2 year follow-up in IRAS (n=134/976) which validates the model developed using MESA according to embodiments of the present invention. The data is based on logistic regression in IRAS with 5-year diabetes conversion (actually 5.2 year conversion) as the dependent variable. Relative predictive values of the 5 regression models are given by the likelihood ratio (LR) $\chi^2$ statistic and area under the ROC curve (AUC). Strengths of association of the indicated variables are given by the odds ratio (OR) per one standard deviation increment. $S_i$ is insulin sensitivity measured by frequently sampled intravenous glucose tolerance testing. FIG. 14 also shows the improved diabetes risk association provided by eLP-IR relative to the prior LP-IR (124.2 versus 119.9) LR$\chi^2$.

FIG. 15 is a chart illustrating the meaning of the interaction parameter based on observed (not predicted) 5-year diabetes conversion rates in 9 subgroups of IRAS participants (all with fasting glucose less than or equal to 110 mg/dL) categorized by their levels (low, intermediate or high by tertile) of GlycA and HDL-P$_{MED}$ according to embodiments of the present invention. For example, when GlycA level is low (bottom tertile), HDL-P$_{MED}$ levels are strongly inversely related to diabetes risk (rates of 2.3% vs 10.1% when HDL-P$_{MED}$ is high vs low, respectively). However, when GlycA level is high (upper tertile), having a high level of HDL-P$_{MED}$ is not good, but actually worse (17.8% conversion rate) than having a low HDL-P$_{MED}$ level (12.9% rate).

Figure 16:
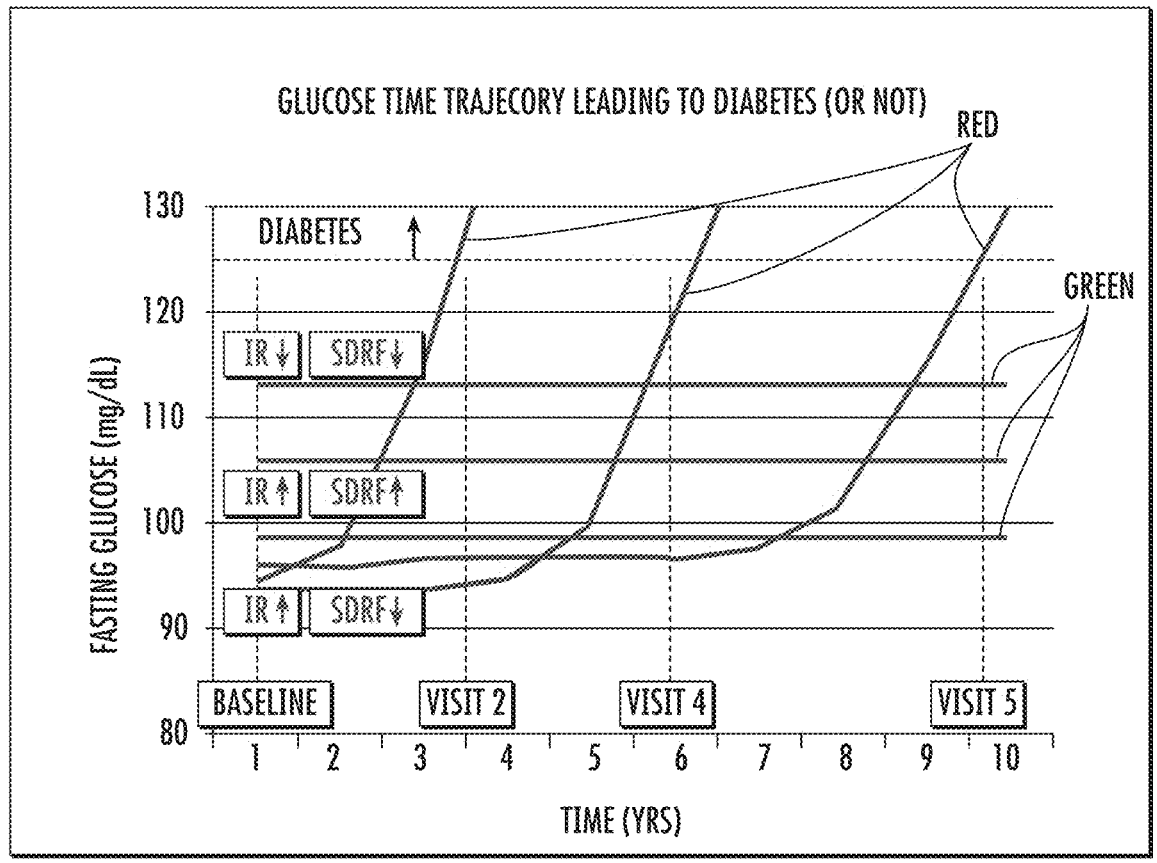
FIG. 16 is an exemplary graph of fasting glucose levels (mg/dL) over time for hypothetical patients with high and low levels of insulin resistance and SDRF to illustrate that SDRF and IR (eLP-IR, for example) can be used to predict whether the glucose value will be stable over time or have a trajectory that leads to diabetes in the future, e.g., either in the short term or longer term according to embodiments of the present invention. The color coding distinguishes those three patients with stable glucose levels over time (green) from those who are likely to convert to diabetes (red).

FIG. 16 is an exemplary graph of fasting glucose (mg/dL) over time (years) for hypothetical patients with high or low levels of insulin resistance (IR) and SDRF score to illustrate that SDRF and IR (eLP-IR, for example) scores can be used with intermediate or low glucose values to predict whether the glucose value will be stable over time or have a trajectory that leads to diabetes in the future, e.g., either in the short term or longer term according to embodiments of the present invention. For example, when both the SDRF score and the IR score are indicated as elevated (e.g., above the 75$^{th}$ percentile), then the glucose trajectory is more likely to rise over a relatively short timeframe, e.g., about 2-3 years or less from the time of the test.

FIG. 17 is an exemplary report which provides a measure of short term risk, e.g., a SDRF score, which may be monitored for change to assess β-cell function/dysfunction over time and provided as a reference or historical segment on the report. A raw STR score in the third tertile or above, e.g., ≥−3.8 (≥75$^{th}$ percentile) could indicate a high risk of converting to diabetes within a relatively short time period, e.g., two years or less post-test.

Figure 20A:
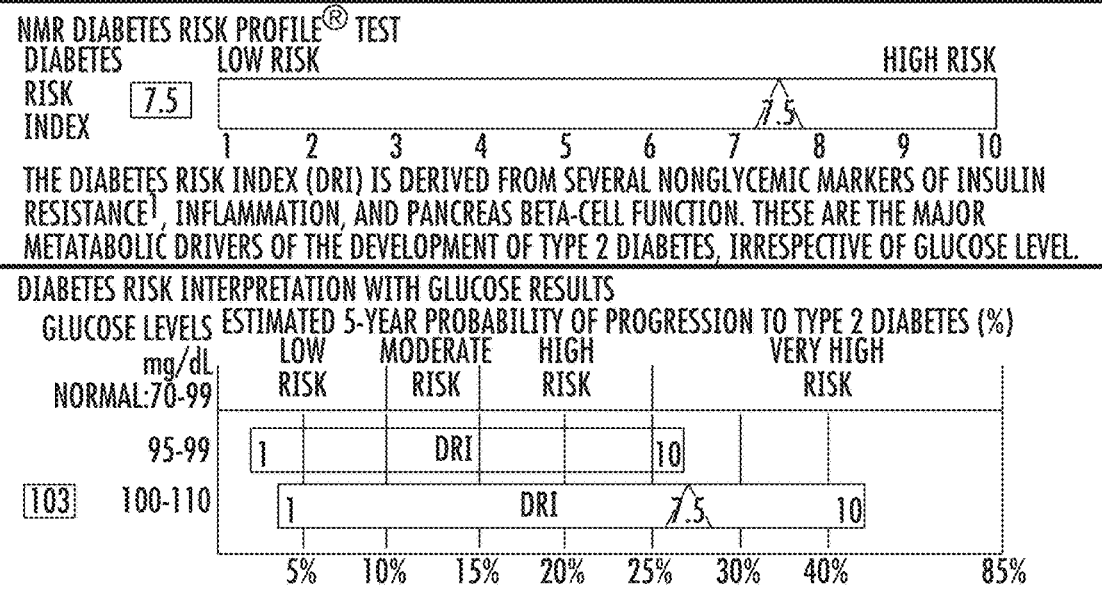
Figure 20B:
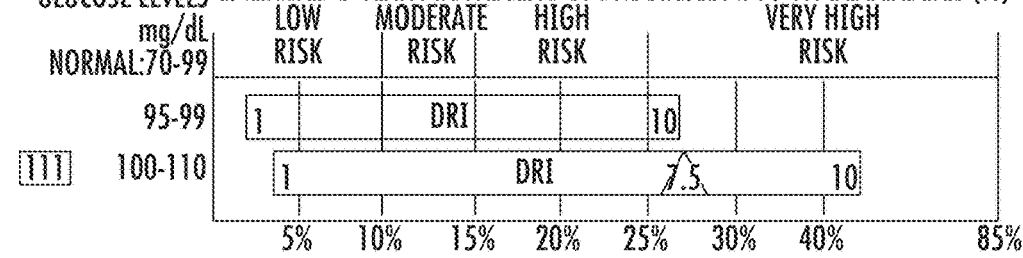

FIGS. 20A-20C are also exemplary reports which provide the same DRI scores with different glucose levels. The reports can also provide separate scores for the inflammatory marker (e.g., GlycA) and a BCAA, e.g., Valine.

The DRI score can also be provided with an associated 5-year risk category. The 5-year risk timeline is believed to be of clinical significance to patients, potentially causing or prompting the patient to take a more active response, e.g., diet, exercise or drug therapy relative to longer timelines. However, longer timelines may be used. The DRI score (e.g., Diabetes Risk Index) can be provide alone or with an interpretation segment with a graph of risk relative to a FPG score of the patient. The historical reporting can correlate the STR or DRI score to the FPG score. Even if the FPG score remains relatively level, the STR, IR or DRI score can indicate a progression toward diabetes if these scores increase.

FIGS. 20A-20C illustrate that patients having the same 7.5 DRI score can have different risks, shown as, very high, high and low 5-year risk category, respectively, based on their FPG level.

Figure 18:
FIG. 18 is a schematic illustration of an exemplary patient report that can provide one or more of a DRI score, IR score (associated with insulin resistance) and STR score (associated with β-cell function) according to embodiments of the present invention.

FIG. 18 is a schematic illustration of an exemplary patient report that can provide one or more of a DRI score, an IR score (associated with insulin resistance) and an STR score (associated with β-cell function) with other lipoprotein and/or metabolite parameters (e.g., the inflammatory marker) according to embodiments of the present invention.

Figure 19:
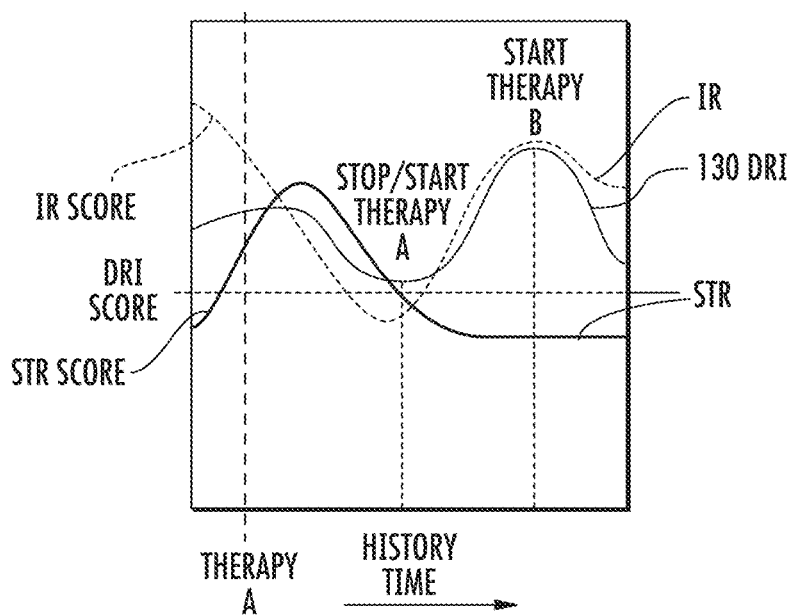
FIG. 19 is an exemplary graph that can be used to evaluate change in one or more of a DRI score, an IR score or an STR scores over time, which may be based or correlated to doses or types of therapies according to embodiments of the present invention.

FIG. 19 is an exemplary graph that can be used to evaluate change in one or more of a DRI score, an IR score or an STR scores over time, which may be based or correlated to doses or types of therapies according to embodiments of the present invention.

The GlycA levels may be measured by NMR in "arbitrary units" that may be converted to methyl group concentration units (umol/L) by multiplying by 17.8.

Figure 21:
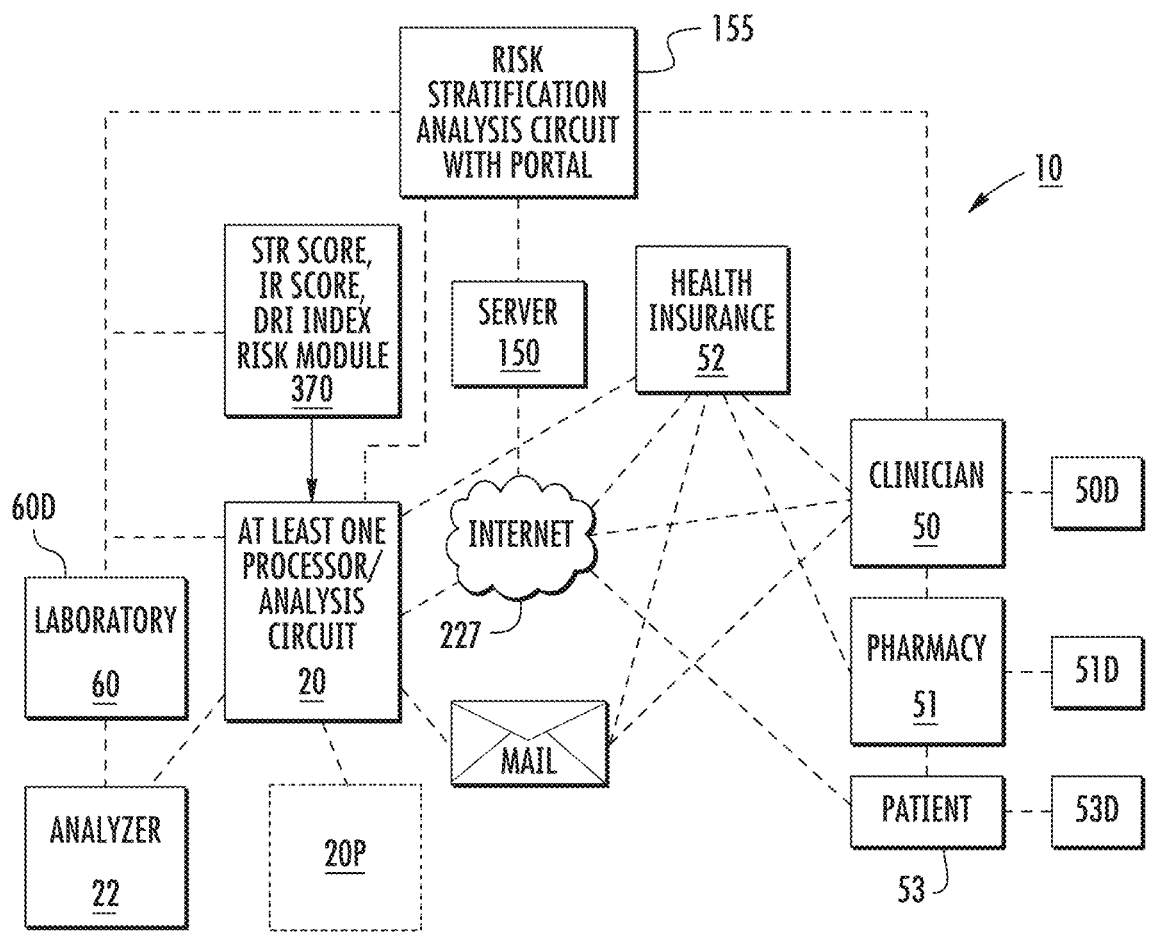
FIG. 21 is a schematic illustration of a system for analyzing a patient's risk using a STR, IR and/or DRI risk index module and/or circuit using according to embodiments of the present invention.

Referring now to FIG. 21, it is contemplated that in some particular embodiments, most, if not all, the measurements for STR, IR and/or DRI scores can be carried out on or using a system 10 in communication with or at least partially onboard an NMR clinical analyzer 22 as described, for example, with respect to FIG. 22 below and/or in U.S. Pat. No. 8,013,602, the contents of which are hereby incorporated by reference as if recited in full herein.

The system 10 can include a STR, IR and/or DRI diabetes risk index (e.g., score) Module 370 to collect data suitable for determining one or all components of the risk scores (e.g., HDL subpopulations, GlycA, Valine). The system 10 can include an analysis circuit 20 that includes at least one processor 20p that can be onboard the analyzer 22 or at least partially remote from the analyzer 22. If the latter, the Module 370 and/or circuit 20 can reside totally or partially on a server 150. The server 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a patient, clinician site 50, which may include an electronic display 50D, to a health insurance agency 52 or a pharmacy 51 and/or the patient 53. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increase risk of an adverse event or to place a medical alert to prevent prescription of a contradicted pharmaceutical agent. The results can be sent to a patient via email to a "home" computer or to a pervasive computing device such as a smart phone or notepad and the like. The results can be as an email attachment of the overall report or as a text message alert, for example.

Still referring to FIG. 21, one or more electronic devices 50D, 51D, 53D, 60D associated with the different users, e.g., a clinician site 50, patient 52D and/or a test or lab site 60 can be configured to access an electronic analysis circuit 155 in communication with a display of a respective electronic device. The analysis circuit 155 can be hosted on a server 150 and can provide an internet portal or downloadable APP or other computer program for various devices. The circuit 155 can configured to allow a user, e.g., a clinician to enter one or more of: (i) a glucose value of a patient, (ii) a glucose value of a patient and a diabetes risk index score, or (iii) a diabetes risk index score. The circuit can automatically populate different data fields based on a patient identifier or other password at sign-in or allow a user to enter one or more of a STR, IR or DRI score and a glucose measurement for a respective patient. The analysis circuit can be configured to track changes in the STR, IR and/or DRI score over time and generate electronic reports that can be sent to clinicians, patients or other users. The analysis circuit can also send notices for recommendations on retests, follow-up tests and the like, e.g., if a STR, IR or DRI risk score is elevated or above a low risk value, e.g., in an intermediate risk category, the circuit can notify the clinician that a glucose test may be appropriate or send a notice to the patient to confer with the doctor to see if a glucose test is appropriate or whether increased monitoring intervals for follow-on DRI tests may be desirable.

The analysis circuit 155 and/or 20 can generate a risk progression pathway or analysis to provide graphic information that stratifies risk of developing type 2 diabetes in the future for patients having the same glucose value when the glucose value is in an intermediate risk range, when fasting plasma glucose levels are between 90-110 mg/dL, A1C % levels are between 5.7-6.4 or oral glucose tolerance levels are between 140-199 mg/dL. The electronic analysis circuit can be onboard the server 150 in the Cloud or otherwise accessible via the Internet 227 or can be associated with a different client architecture as will be appreciated by one of skill in the art. Thus, a clinician, patient or other user can generate a customized report on risk progression or otherwise obtain risk stratification information.

Figure 22:
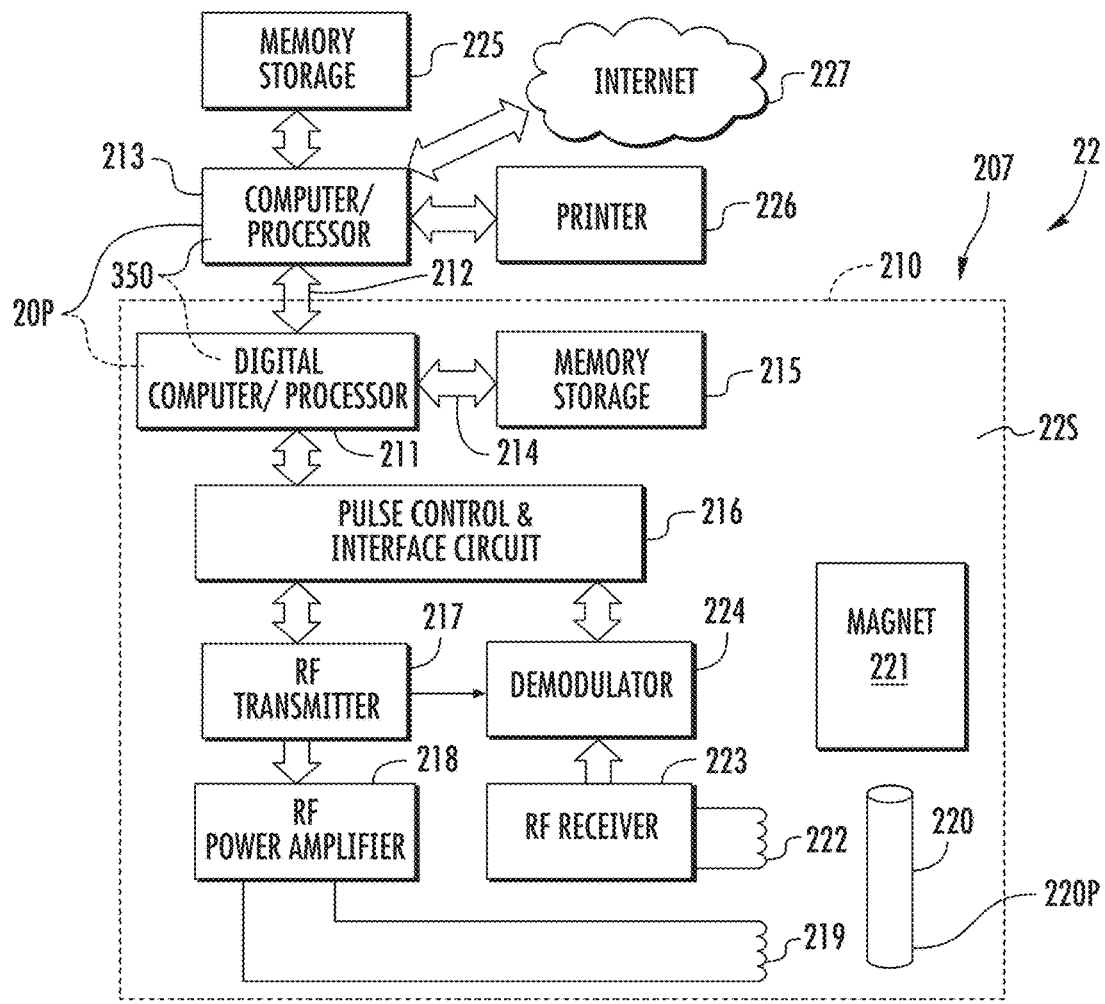
FIG. 22 is a schematic illustration of a NMR spectroscopy apparatus according to embodiments of the present invention.

Referring now to FIG. 22, a system 207 for acquiring at least one NMR spectrum for a respective biosample is illustrated. The system 207 includes an NMR spectrometer 22s and/or analyzer 22 for obtaining NMR data for NMR measurements of a sample. In one embodiment, the spectrometer 22s is configured so that the NMR signal acquisition is conducted at about 400 MHz for proton signals; in other embodiments the measurements may be carried out at between about 200 MHz to about 900 MHz or other suitable frequency. Other frequencies corresponding to a desired operational magnetic field strength may also be employed. Typically, a proton flow probe is installed, as is a temperature controller to maintain the sample temperature at 47+/− 0.5 degrees C. The spectrometer 22s can be controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215 and/or remote server 150 (FIG. 15).

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220 and/or flow probe 220p. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The diabetes risk evaluation Module 370 or analysis circuit 20, 155 (FIG. 21) or can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory, the computer 213, which may be a personal, laptop, desktop, workstation, notepad, tablet or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Embodiments of the present invention may take the form of an entirely software embodiment or an embodiment combining software and hardware aspects, all generally referred to herein as a "circuit" or "module."

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN) or secured area network (SAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 23:
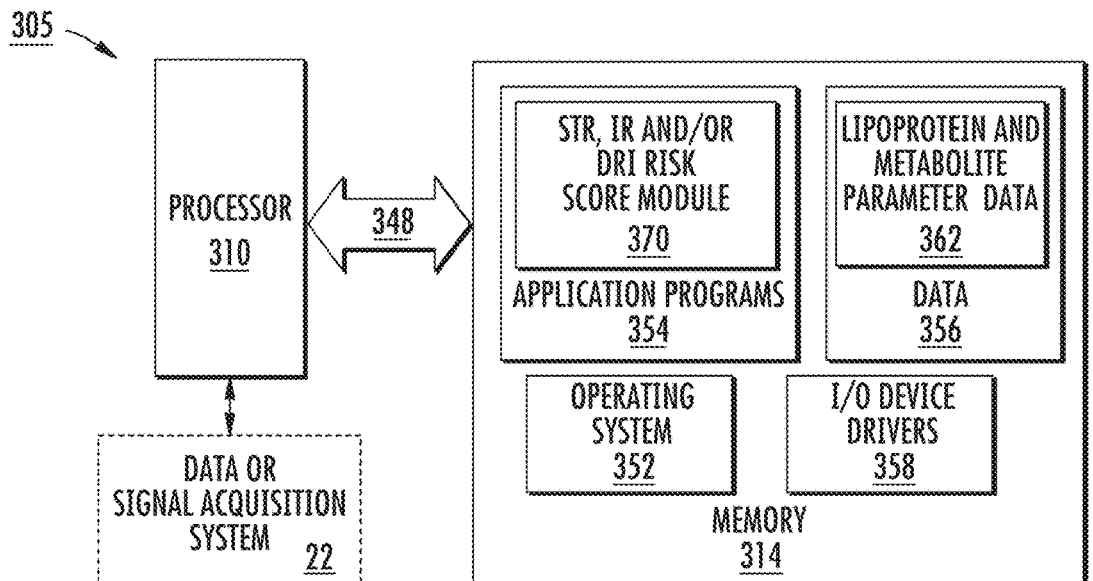
FIG. 23 is a schematic diagram of a data processing system according to embodiments of the present invention.

FIG. 23 is a block diagram of exemplary embodiments of data processing systems 305 that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 23, the memory 314 may include several categories of software and data used in the data processing system 305: the operating system 352; the application programs 354; the input/output (I/O) device drivers 358; an STR, IR and/or DRI risk score module 370 and the data 356. The Module 370 can consider the level of defined metabolite and lipoprotein parameters of the defined multi-marker STR and IR parameters which can include a measurement of GlycA, lipoprotein components and Valine and also optionally, glucose, in a multi-parameter mathematical model of risk of developing type 2 diabetes in a defined timeline, e.g., the next 5 years or a likelihood of having prediabetes.

The data 356 may include signal (constituent and/or composite spectrum lineshape) or measurement data of the lipoproteins and metabolite parameters 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the analyzer 22. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 370 being an application program in FIG. 23, as will be appreciated by those of skill in the art, other configurations may also be utilized while still benefiting from the teachings of the present invention. For example, the Module 370 may also be incorporated into the operating system 352, the I/O device drivers 358 or other such logical division of the data processing system 305. Thus, the present invention should not be construed as limited to the configuration of FIG. 23, which is intended to encompass any configuration capable of carrying out the operations described herein.

Figure 24:
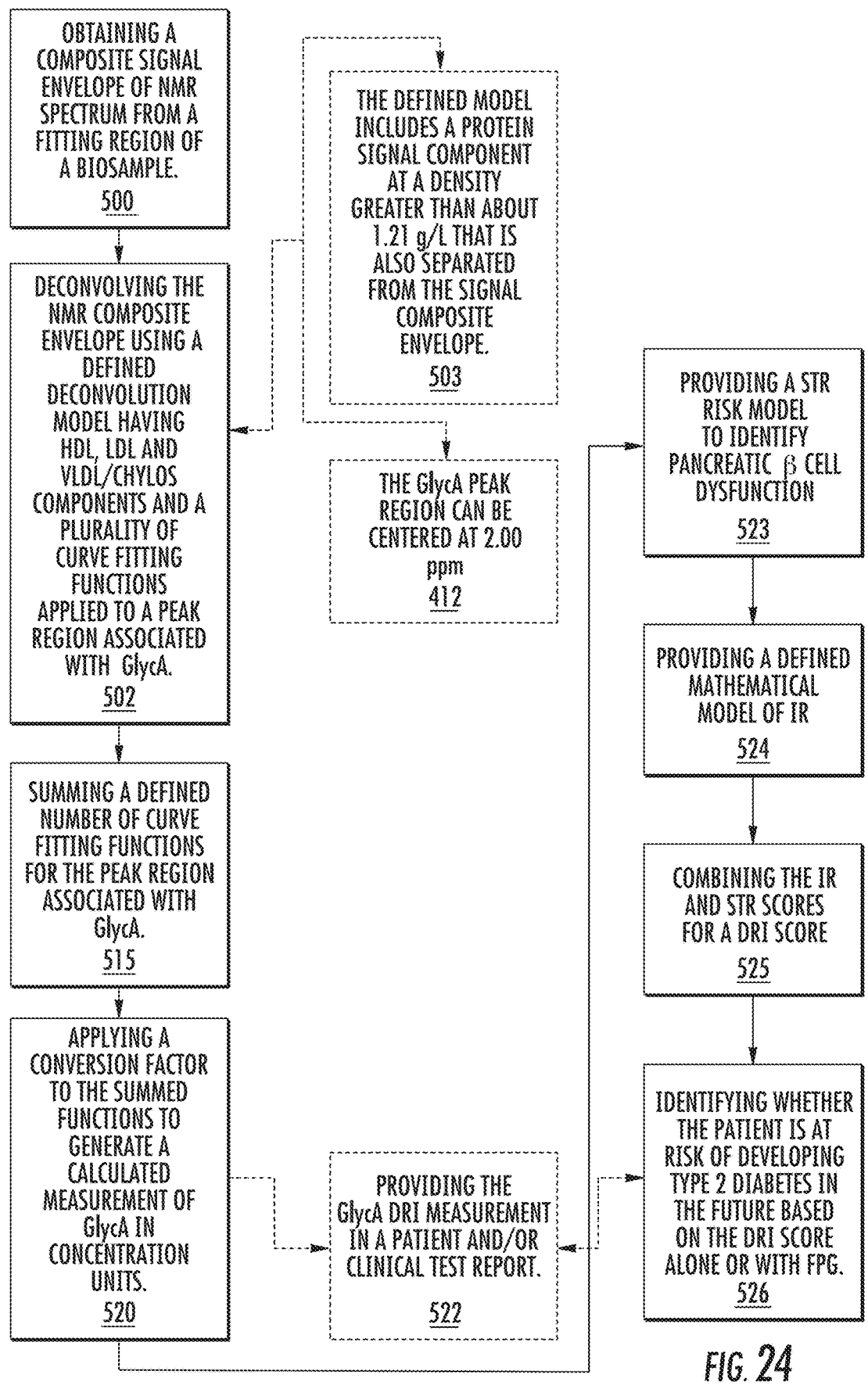
FIG. 24 is a flow chart of exemplary operations that can be used to assess a risk of developing T2DM in the future and/or having prediabetes, according to embodiments of the present invention.

FIG. 24 is a flow chart of exemplary operations that can carry out embodiments of the present invention. In some embodiments, the inflammatory marker is an NMR derived GlycA which can employ actions associated with blocks 500, 502, 515, 520 and optionally 503, 412 and 522. However, where other inflammatory markers are used, the methods can include only blocks, 423, 524, 525 and 526, according to some embodiments.

If GlycA is the inflammatory marker, the method can include obtaining a (measured) composite envelope NMR spectrum of NMR spectra of a fitting region of a biosample (e.g., blood plasma or serum) can be obtained (block 500). The NMR composite signal envelope is electronically deconvolved using a defined model having HDL, LDL and VLDL/Chylos components and a plurality of curve fit (e.g., Lorentzian) functions associated with at least a GlycA peak region centered at a defined chemical shift location (e.g., 2.00 ppm) associated with GlycA (block 502). A defined number of curve fitting functions for the peak region associated with GlycA can be summed (block 515). A conversion factor can be applied to the summed functions to generate a calculated measurement of GlycA (block 520).

The method can include providing a STR risk factor score to identify potential β-cell dysfunction and/or impairment or a change in β-cell status (block 523). The change in status can be an improvement or further impairment associated with a therapy, such as a drug therapy, for example.

The method can include providing an IR risk score associated with insulin resistance and the risk of conversion or progression to type 2 diabetes, typically within 5-7 years (block 524).

The method can include combining the IR and STR scores (block 525) and identifying whether the patient is at risk of developing type 2 diabetes and/or has prediabetes based on the combined IR and STR scores as a DRI score (block 526). The IR score may be weighted to have an increased value relative to its un-weighted score to provide a greater input into the DRI score relative to the STR score or may naturally have a more dominant score in longer term evaluations.

The STR and IR scores can be generated using defined models of risk with associated defined coefficients for defined lipoprotein and metabolite parameters to generate STR and IR scores that generate a DRI score in a range between 1-10.

Optionally, the DRI and/or GlycA scores can be provided in a patient and/or clinical trial report (block 522).

The defined GlycA deconvolution model can include a protein signal component at a density greater than about 1.21 g/L that can be deconvolved/separated from the signal composite envelope (block 503).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of evaluating a subject's risk of developing type 2 diabetes and/or having pancreatic beta cell impairment and/or dysfunction, comprising:
performing Nuclear Magnetic Resonance spectroscopy on a biosample from the subject to measure a concentration of a defined high density lipoprotein particle (HDL-P) subpopulation and a concentration of GlycA;
programmatically calculating a short term diabetes risk factor (SDRF) score of a subject using a defined mathematical model; and
comparing the calculated SDRF score to a SDRF score of a study population,
wherein the defined mathematical model includes a concentration measurement of a defined high density lipoprotein particle (HDL-P) subpopulation, a concentration measurement of inflammatory marker GlycA to generate the calculated SDRF score.

2. The method of claim 1, wherein the defined HDL-P subpopulation is medium HDL-P.

3. The method of claim 2, further comprising an interaction parameter of GlycA multiplied by the concentration of medium HDL-P, wherein the subject is at risk of beta cell dysfunction when medium HDL-P and GlycA values are in a third tertile values of the population norm.

4. The method of any of claim 1, further comprising programmatically calculating an insulin resistance (IR) score of the subject using a defined mathematical model of insulin resistance.

5. The method of claim 4, wherein the defined mathematical model of insulin resistance for the IR score includes a plurality of components including a concentration measurement of a defined HDL-P subpopulation, a concentration measurement of GlycA, a concentration measurement of a defined subpopulation of VLDL-P (very low density lipoprotein/chylomicron particle subclasses), an IR index with a range of between 0-100, the range representing from low to high, insulin sensitivity to insulin resistance, and a concentration measurement of a branched chain amino acid (BCAA), obtained from the biosample of the subject.

6. The method of claim 5, wherein the components of the defined mathematical model of insulin resistance are mathematically combined to generate the IR score.

7. The method of claim 5, wherein the measurement of the defined sub-population of VLDL-P is a concentration of medium VLDL-P, and wherein the BCAA is Valine.

8. The method of claim 4, further comprising programmatically calculating a diabetes risk score by combining the SDRF score and the IR score.

9. The method of claim 8, wherein coefficients of the SDRF and IR scores are derived from a logistic regression model that includes SDRF and IR to predict actual 5 year conversion to diabetes using at least one defined population study to thereby generate a DRI score with a risk of conversion within 5 years irrespective of a glucose value of the subject.

10. The method of any of claim 9, further comprising evaluating a measured glucose and/or HbA1c value of the subject, and electronically providing a report with a 5 year risk of conversion to Type 2 diabetes risk estimate based on the glucose measurement and the DRI score.

11. The method of claim 4, wherein the IR score is an eLP-IR score and is calculated using the following equation:

eLP-IR=(A) (LP-IR)+(B)(Valine)−(C) (VLDL-$P_{MED}$)−(D)(HDL-$P_{MED}$)+(E)(GlycA), wherein A, B, C, D and E are defined beta coefficients from a linear regression model for insulin resistance, HDL-$P_{mED}$ is the concentration of a medium HDL-P subpopulation, VLDL-$P_{MED}$ is a concentration of a medium VLDL-P subpopulation, valine is a branched chain amino acid, and LP-IR is a lipoprotein insulin resistance index calculated using six defined lipoprotein subclasses and has a numerical value in a range of 0-100 representing insulin sensitive to insulin resistance.

12. The method of any of claim 4, further comprising generating a DRI score using the following equation:

DRI score=X(IR score)+Y(SDRF), wherein X and Y are coefficients defined by a logistic regression model for 5-year diabetes conversion in people with glucose <110 mg/dL using a defined study population, and wherein the DRI score is mathematically altered into a range of between 0-10 or 1-10 or 0-100 or 1-100 using a plurality of equal subparts over a range of possible DRI raw scores.

13. The method of any of claim 1, wherein the SDRF score is calculated using the following equation:

SDRF score=−(A) (HDL-$P_{MED}$)−(B) (GlycA)+(C) (GlycA×HDL-$P_{MED}$), wherein A, B and C are defined beta coefficients from a logistic regression model for short term conversion to diabetes as the defined mathematical model of risk of developing type 2 diabetes, and HDL-$P_{MED}$ is a medium size HDL-P subpopulation, and GlycA χHDL-$P_{MED}$ an interaction parameter.

14. The method of claim 1, further comprising at least one of: evaluating a drug therapy, evaluating a clinical trial, or evaluating candidates for drug discovery, using the SDRF score.

15. The method of claim 1, further comprising calculating a plurality of the SDRF scores over time from respective biosamples to thereby evaluate a change in SDRF score to identify a change in β-cell dysfunction.

16. The method of claim 1, wherein raw scores associated with the SDRF score are between −6.4 and −1.6, wherein −4.1 is associated with about a 25th percentile and >−3.8 is associated with about >75th percentile of the study population, and wherein >−3.8 values indicate an increased risk of beta cell dysfunction and/or early conversion to type 2 diabetes independent of glycemic value that can stratify risk of conversion to type 2 diabetes for subjects having a common glycemic measurement with different SDRF scores.

17. The method of claim 1, wherein the SDRF score is provided in a report in a defined numerical score range, with scores associated with a fourth quartile (4Q), fifth quintile (SQ) or 10th decile of the study population reflecting an increased risk of developing type 2 diabetes within 2 years and/or beta cell dysfunction and/or impairment relative to scores in a first quartile, quintile or decile of the population.

18. The method of claim 1, wherein the HDL-P subpopulation comprises only medium HDL particle subclasses with diameters between 8.3 nm and 9.4 nm, between 8.3 nm and 10.0 nm, or between 8.3 nm and 10.2 nm.

19. A method of identifying at-risk patients that may benefit from therapies for improving or stabilizing beta-cell function and/or improve a patient's ability to produce insulin, comprising:
performing Nuclear Magnetic Resonance spectroscopy on a biosample from a subject to measure concentrations of GlycA and defined lipoprotein and metabolite components; and
electronically generating a short term risk (STR) score by combining measurements of defined lipoprotein and metabolite components of a biosample of a subject, wherein the components include a high density lipoprotein particle (HDL-P) subpopulation and an interaction parameter using the concentration measurements of the HDL-P subpopulation and GlycA.

20. A method of identifying subjects that are likely to benefit from a drug therapy such as reconstituted HDL infusion for improving pancreatic beta cell function and/or to inhibit Type 2 diabetes mellitus (T2DM), comprising:
performing Nuclear Magnetic Resonance on a biosample from a subject to measure concentrations of GlycA and defined lipoprotein and metabolite components;
generating a defined short term diabetes risk factor (SDRF) score using measurements of defined lipoprotein and metabolite components of a biosample of a subject, wherein the components include a high density lipoprotein particle (HDL-P) subpopulation and GlycA; and
comparing the generated SDRF score to the SDRF score of a defined population norm to identify if a subject is likely to benefit from therapy to improve pancreatic beta cell function and/or inhibit T2DM.

* * * * *